US007732601B2

(12) United States Patent
Szczepek et al.

(10) Patent No.: US 7,732,601 B2
(45) Date of Patent: Jun. 8, 2010

(54) CRYSTALLINE POLYMORPHS OF METHANESULFONIC ACID ADDITION SALTS OF IMATINIB

(75) Inventors: Wojciech Szczepek, Warsaw (PL); Dorota Samson-Lazinska, Warsaw (PL); Bogdan Zagrodzki, Warsaw (PL); Magdalena Glice, Warsaw (PL); Wioleta Maruszak, Warsaw (PL); Katarzyna Korczak, Warsaw (PL); Ryszard Modzelewski, Warsaw (PL); Marta Lawecka, Warsaw (PL); Lukasz Kaczmarek, Warsaw (PL); Wieslaw Szelejewski, Warsaw (PL); Urszula Fraczek, Marki (PL); Piotr Cmoch, Warsaw (PL)

(73) Assignee: Instytut Farmaceutyczny, Warsaw (PL)

( * ) Notice: Subject to any disclaimer, the term of this patent is extended or adjusted under 35 U.S.C. 154(b) by 298 days.

(21) Appl. No.: 10/599,461

(22) PCT Filed: Apr. 2, 2005

(86) PCT No.: PCT/PL2005/000024

§ 371 (c)(1), (2), (4) Date: Sep. 29, 2006

(87) PCT Pub. No.: WO2005/095379

PCT Pub. Date: Oct. 13, 2005

(65) Prior Publication Data

US 2007/0197545 A1 Aug. 23, 2007

(30) Foreign Application Priority Data

Apr. 2, 2004 (PL) .................................... 366885
Apr. 1, 2005 (PL) .................................... 374074

(51) Int. Cl.
*C07D 401/14* (2006.01)
*C07D 403/14* (2006.01)
*A61P 35/00* (2006.01)

(52) U.S. Cl. .................................................... 544/295

(58) Field of Classification Search ................. 544/295
See application file for complete search history.

(56) References Cited

FOREIGN PATENT DOCUMENTS

WO 99/03854 1/1999
WO 2004/026930 A2 4/2004

*Primary Examiner*—James O Wilson
*Assistant Examiner*—Cecilia M Jaisle
(74) *Attorney, Agent, or Firm*—Matthias Scholl, PC; Matthias Scholl

(57) ABSTRACT

This invention relates to the methanesulfonic acid addition salts of Imatinib and to the synthesis thereof. In particular, this invention relates to the synthesis of crystalline $\alpha$-form of Imatinib methanesulfonate. Furthermore, the invention is directed to a novel acid addition salt of 4-(4-methylpiperazin-1-ylmethyl)-N-[4-methyl-3-[(4-pyridin-3-yl)pyrimidin-2-ylamino)phenyl]benzamide with two molecules of methanesulfonic acid and to the polymorphic forms thereof, as well as to their pharmaceutical compositions.

18 Claims, 12 Drawing Sheets

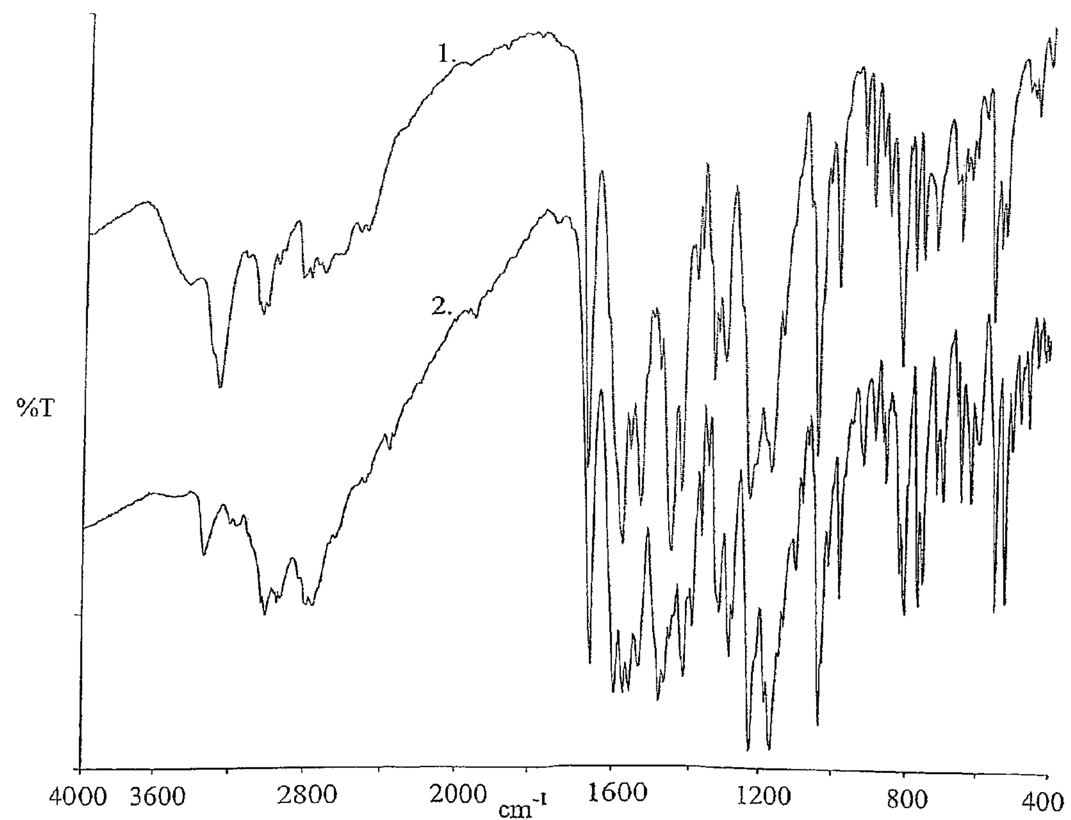
Fig. 1. FT-IR (KBr):
1. Imatinib monomesylate Form α;
2. Imatinib monomesylate Form β.

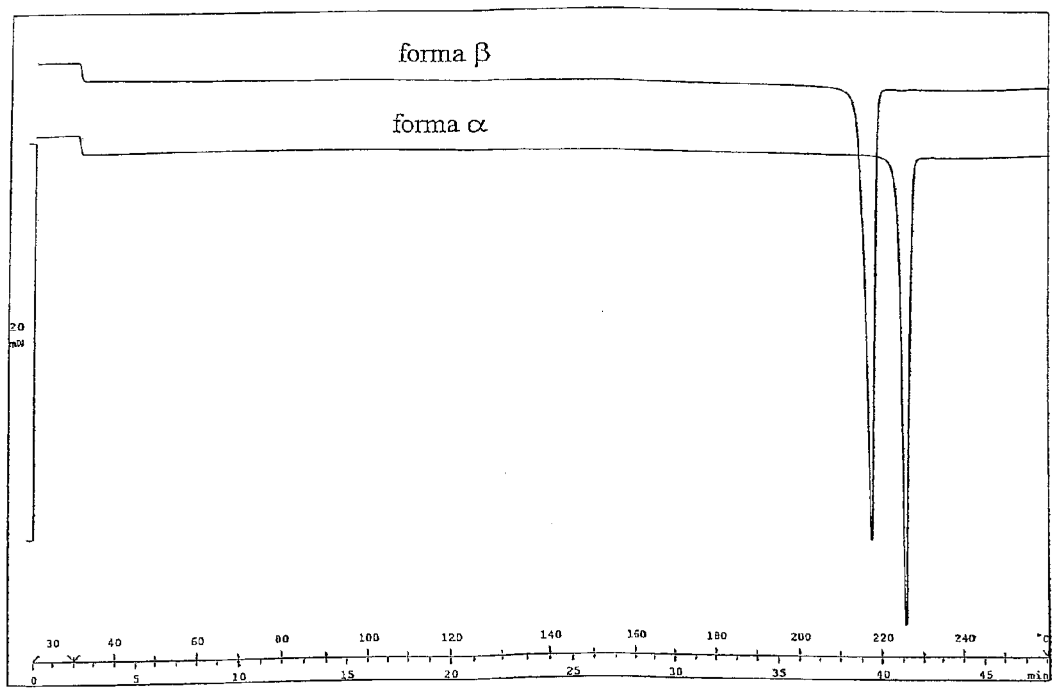
Fig.2. DSC: Imatinib monomesylate Forms α and β.

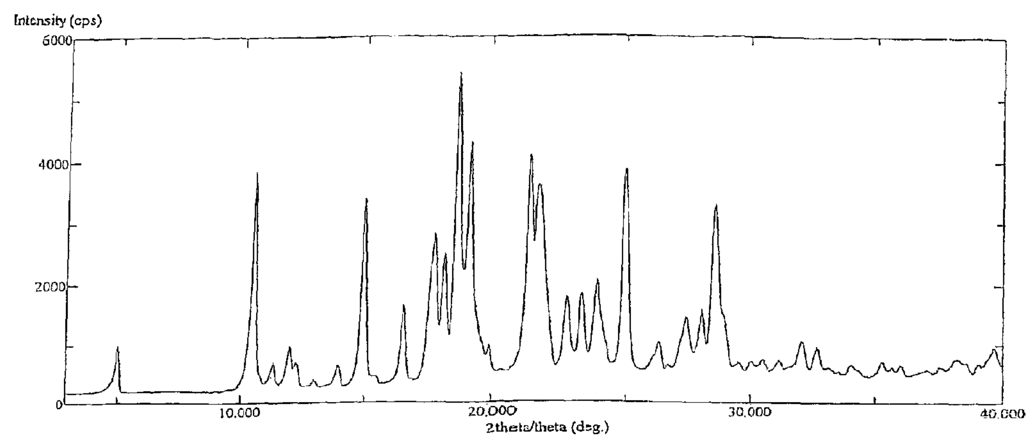
Fig. 3. XRPD: Imatinib monomesylate Form α.
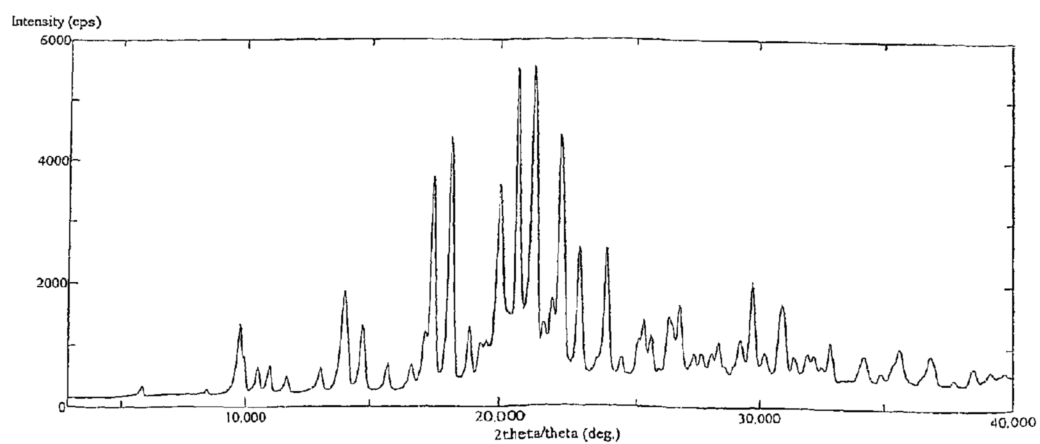
Fig. 4 XRPD: Imatinib monomesylate Form β.

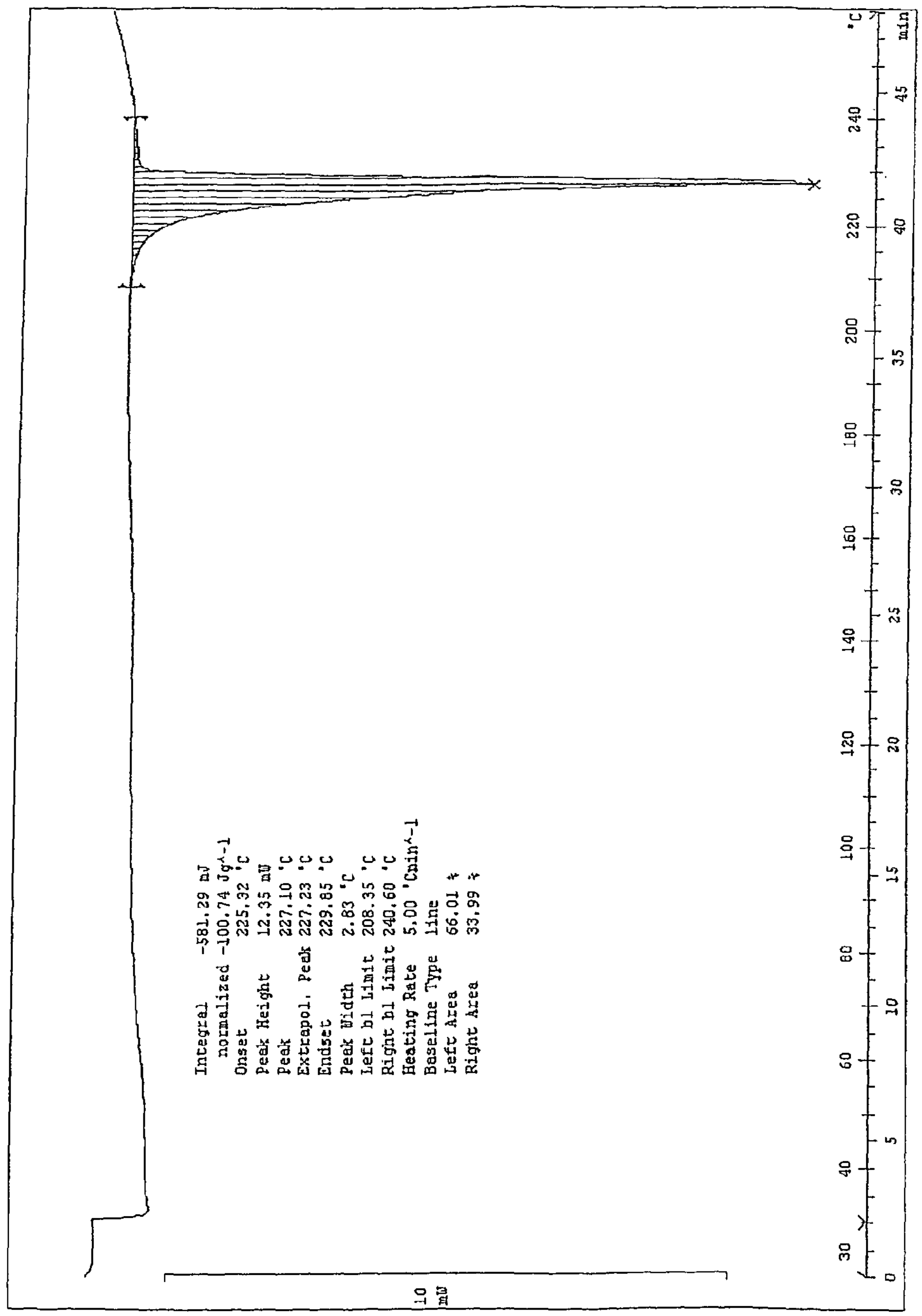
Fig. 5. DSC: Imatinib dimesylate Form I.

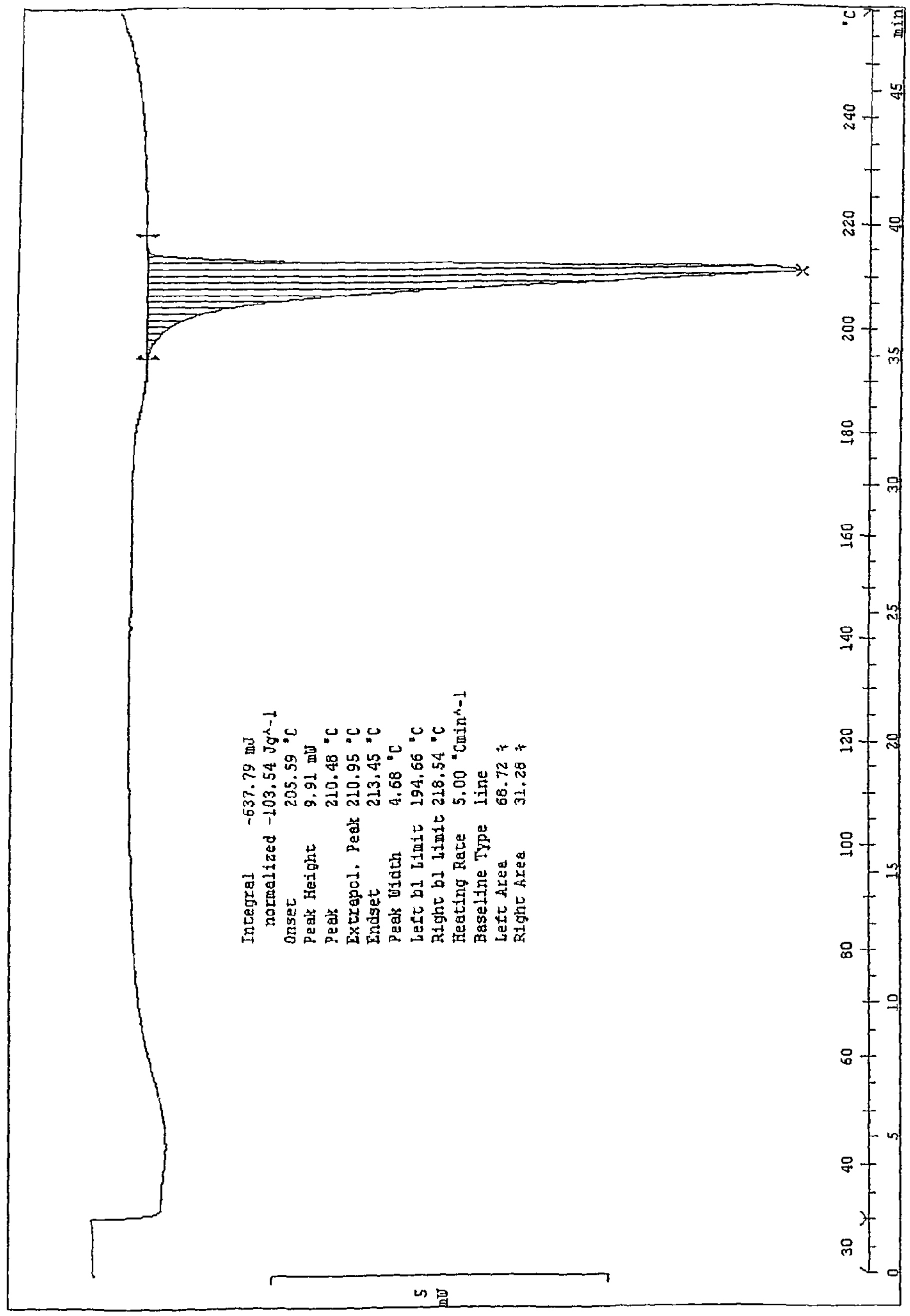
Fig. 6. DSC: Imatinib dimesylate Form II.

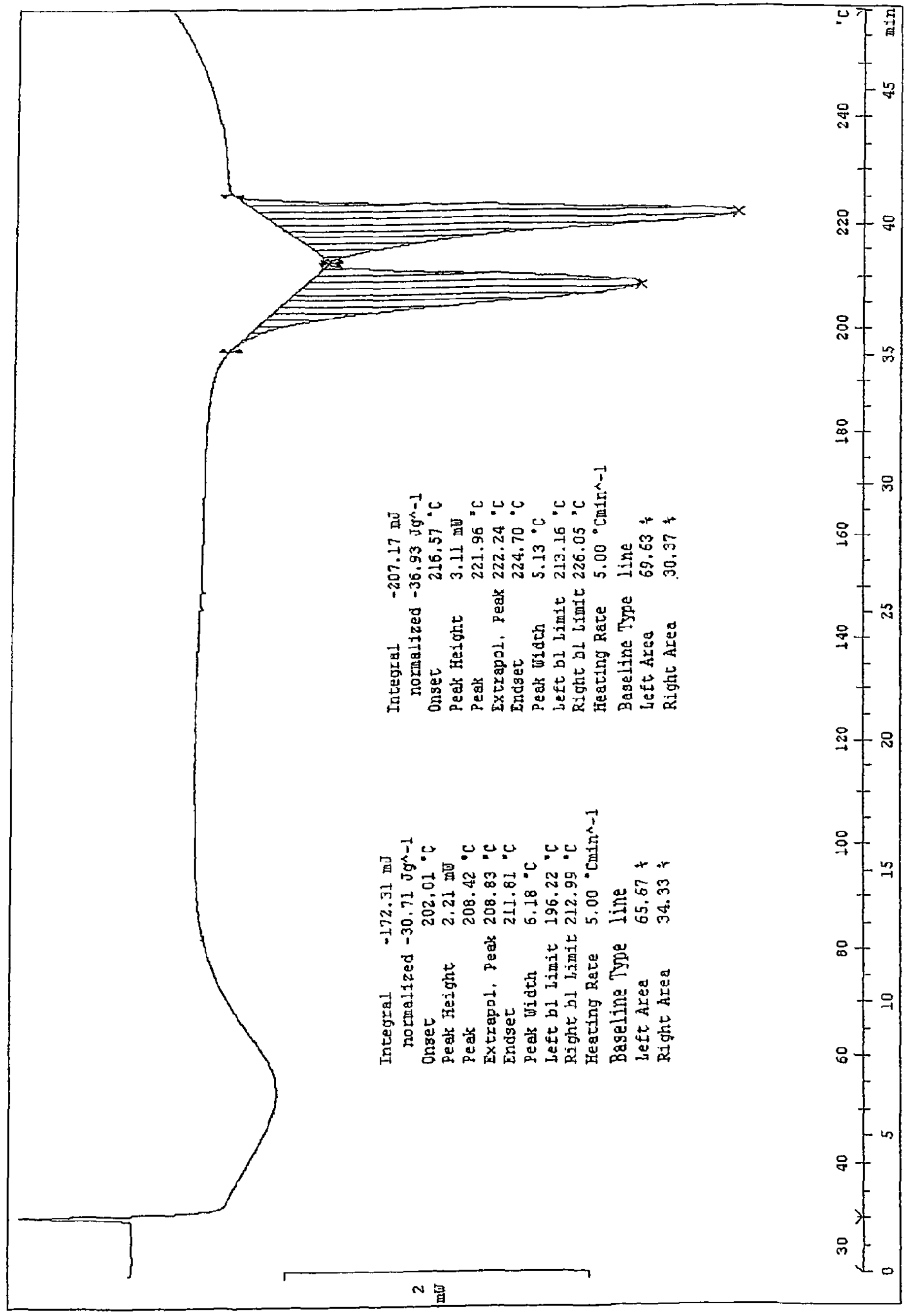
Fig. 7. DSC: Imatinib dimesylate, Forms I and II (~ 1:1).

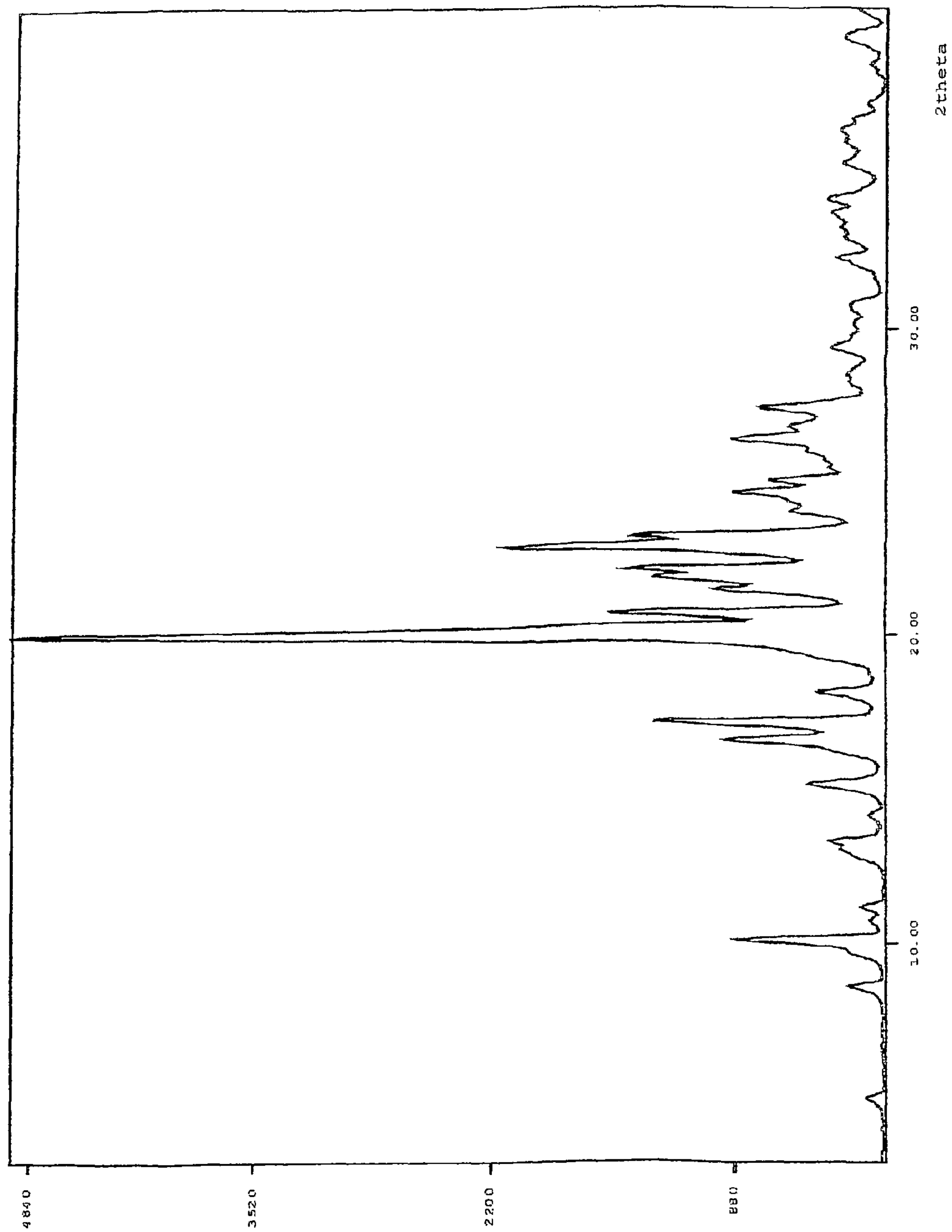
Fig. 8. XRPD: Imatinib dimesylate Form I.

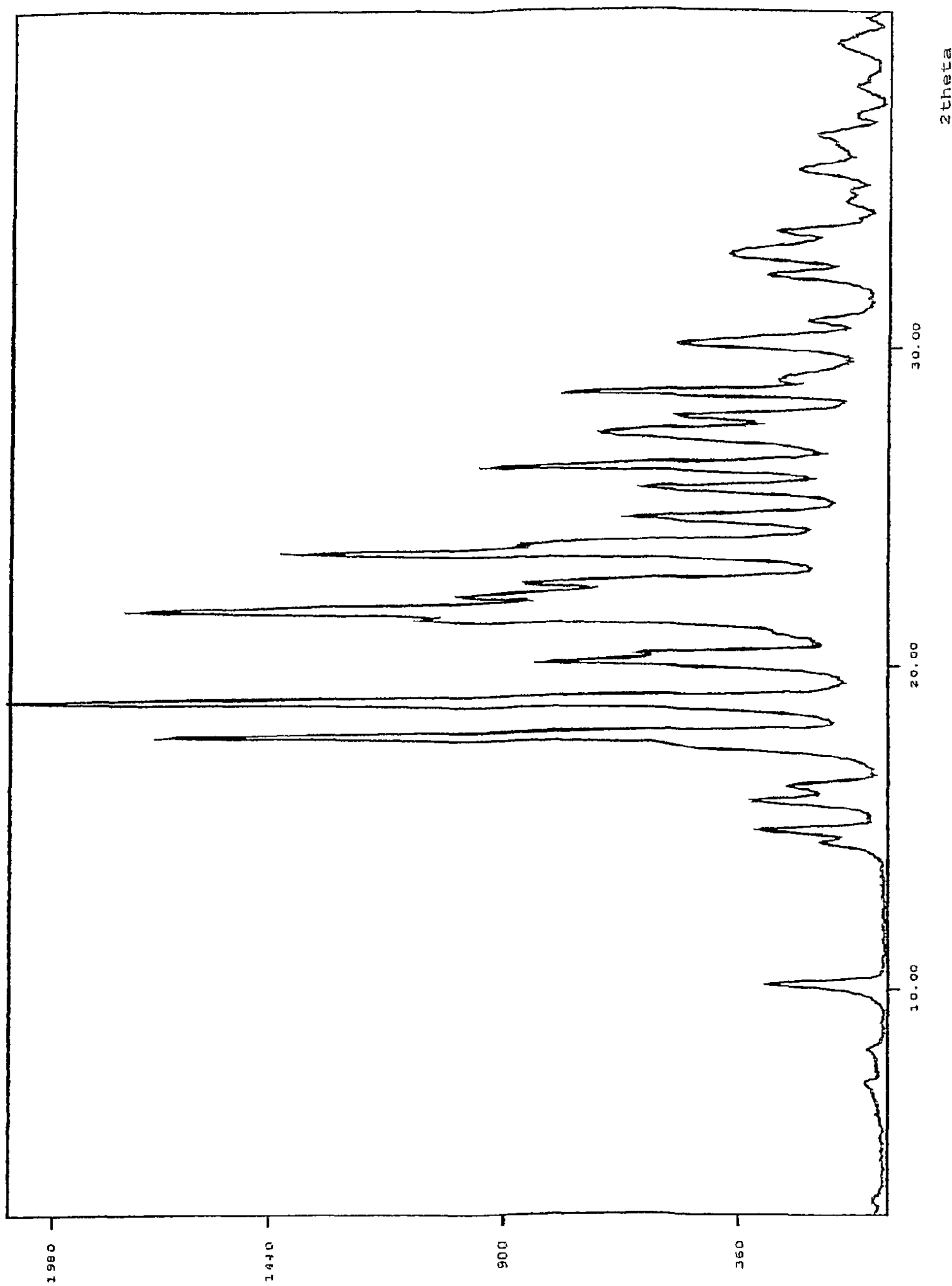
Fig.. 9. XRPD: Imatinib dimesylate Form II.

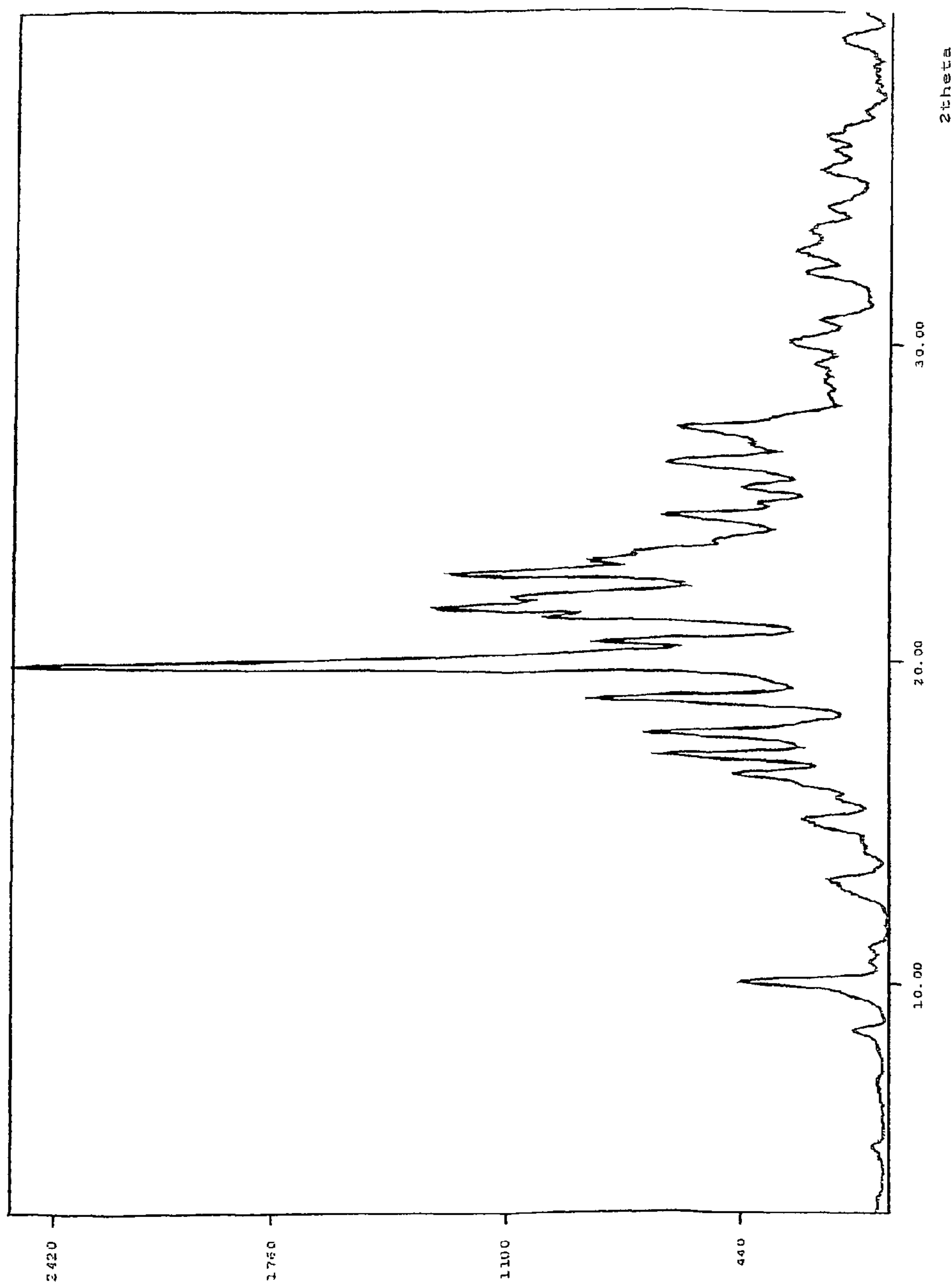
Fig..10. XRPD: Imatinib dimesylate, Forms I and II (~ 1:1).

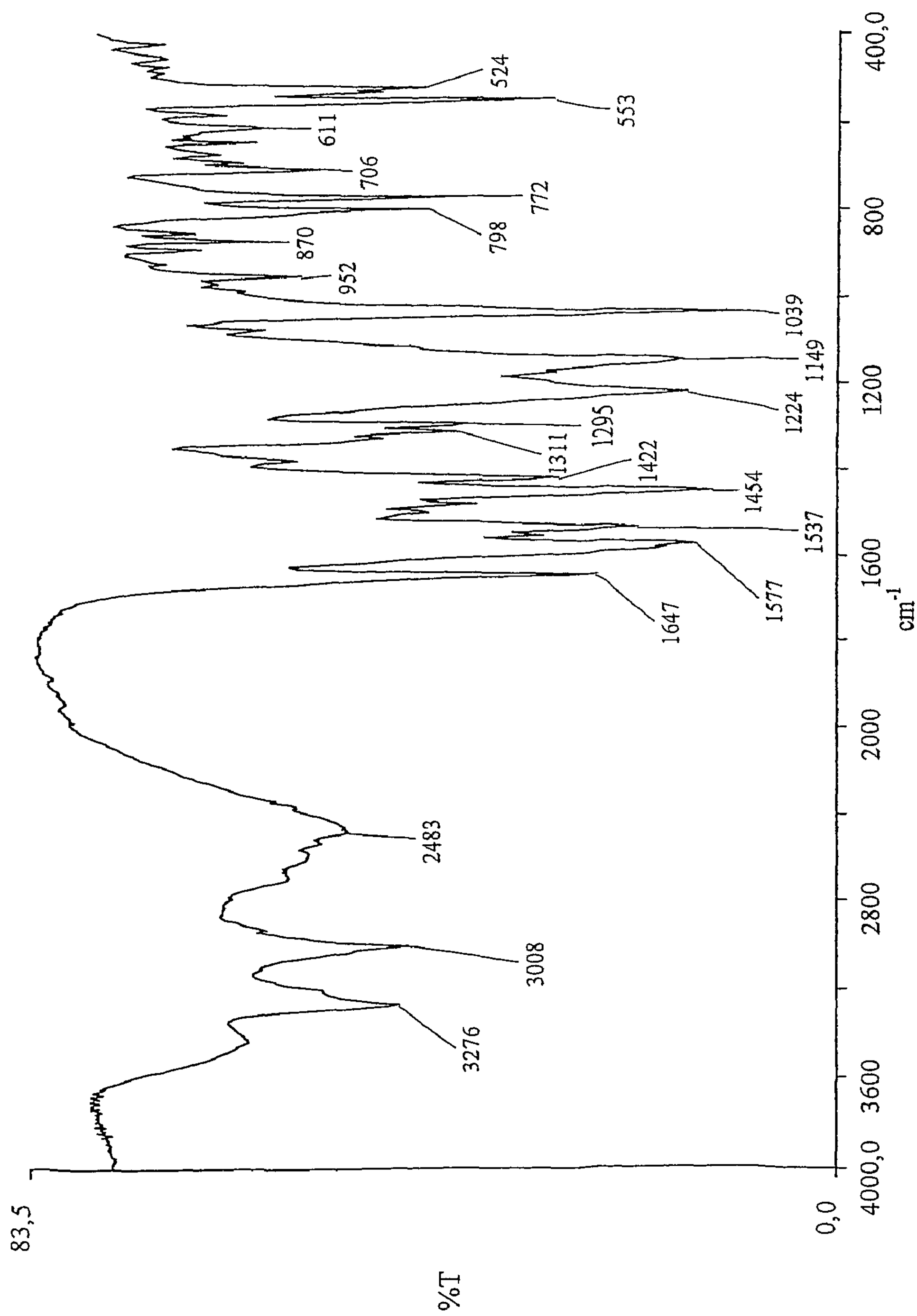
Fig. 11. FT-IR (KBr): Imatinib dimesylate Form I.

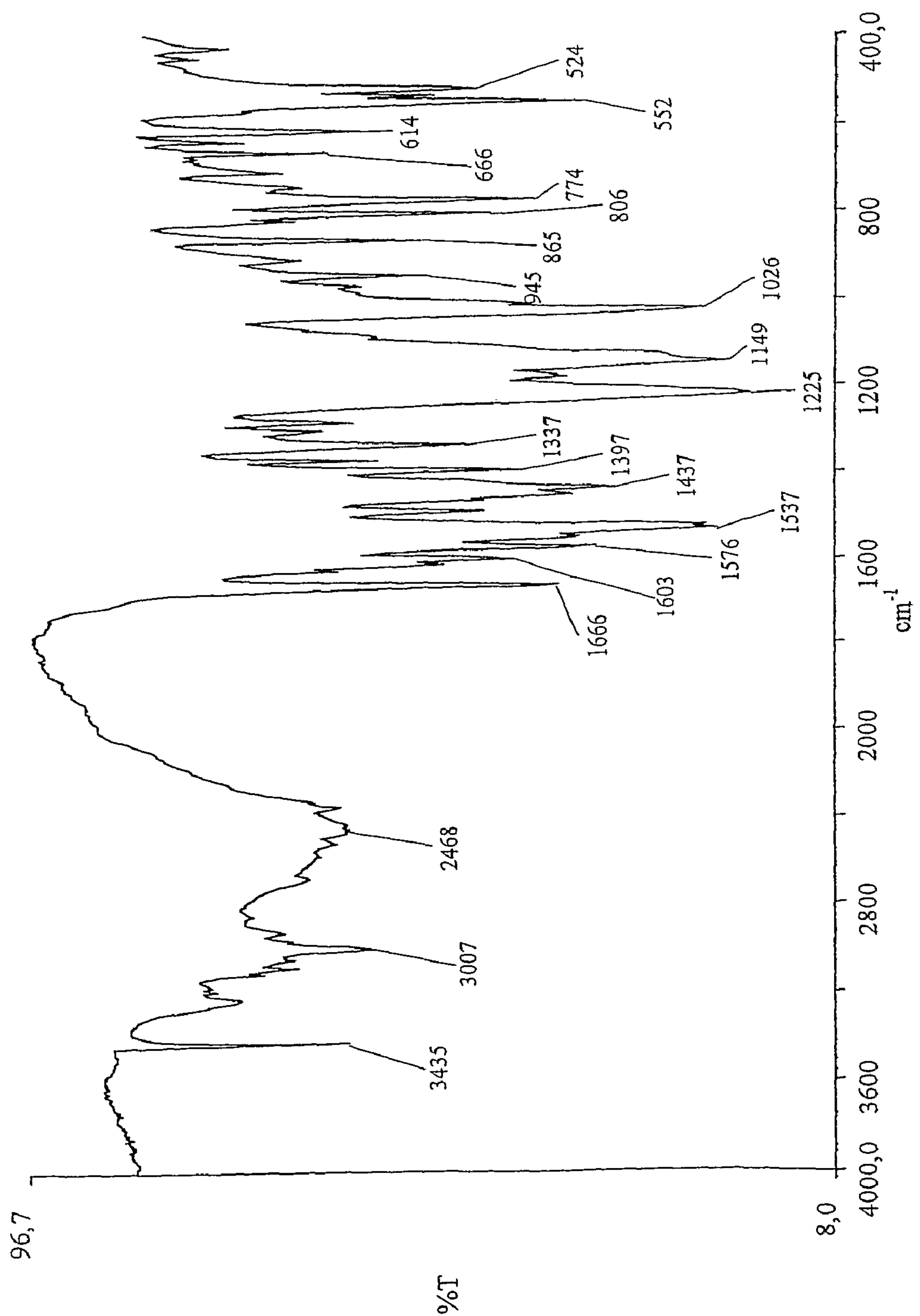
Fig. 12. FT-IR (KBr): Imatinib dimesylate Form II.

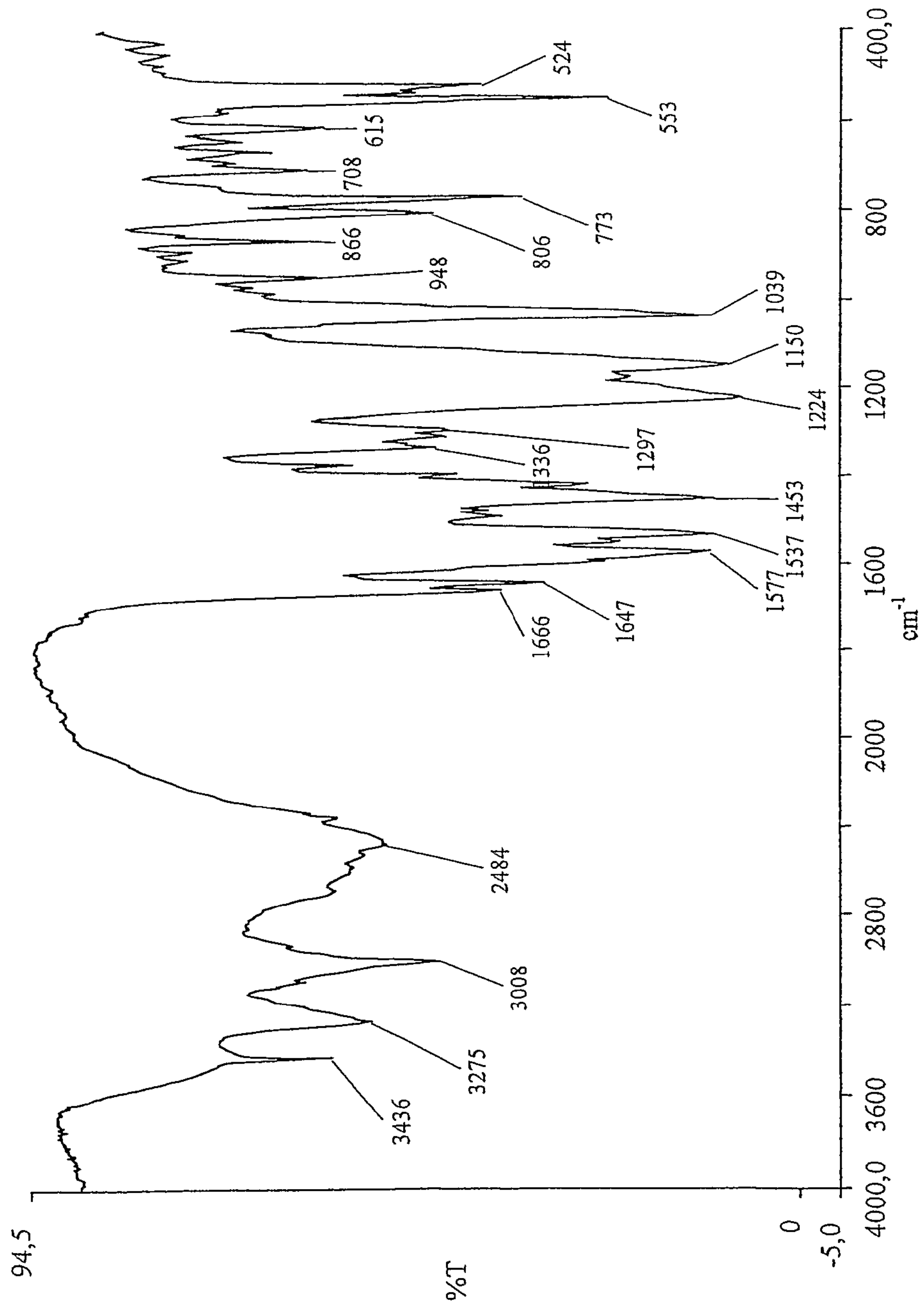
Fig. 13. FT-IR (KBr): Imatinib dimesylate, Forms I and II (~ 1:1).

CRYSTALLINE POLYMORPHS OF METHANESULFONIC ACID ADDITION SALTS OF IMATINIB

CROSS-REFERENCE TO RELATED APPLICATIONS

This is a National Stage Application of International Patent Application No. PCT/PL 2005/000024, with an international filing date of Apr. 2, 2005, which is based on Polish Patent Application No. P-366885, filed Apr. 2, 2004 and Polish Patent Application No. P-374074, filed Apr. 1, 2005. The contents of all of these applications are incorporated herein by reference.

BACKGROUND OF THE INVENTION

1. Field of the Invention

The invention relates to crystalline polymorphs of methanesulfonic acid addition salts of Imatinib and to the synthesis thereof, and in particular to the synthesis of the α-crystal form of Imatinib mesylate.

2. Description of the Related Art

Imatinib, 4-(4-methylpiperazin-1-ylmethyl)-N-[4-methyl-3-[(4-pyridin-3-yl)pyrimidin-2-yloamino]phenyl]benzamide, has been disclosed in the European Patent Application EP 0564409 A1 as a pharmacologically active substance having anti-tumor activity, especially useful in the treatment of diseases which respond to inhibition of tyrosine kinase receptors.

International Patent Publication WO 2004/026930 relates to the use of Imatinib or a pharmaceutically acceptable salt thereof for reducing inflammation. Although the use of many pharmaceutically-acceptable acid addition salts of Imatinib is mentioned including methanesulfonic acid salts of Imatinib, experimental studies are described in detail only with respect to the monomethanesulfonate salt thereof.

A novel crystal modification of the methanesulfonic acid addition salt of 4-(4-methylpiperazin-1-ylmethyl)-N-[4-methyl-3-[(4-piperidin-3-yl)pyrimidin-2-ylamino]phenyl]benzamide, i.e. the β-crystal form, has been described in the International Patent Publication WO 99/03854. The β-crystal form could be obtained, inter alia, from the less thermodynamically stable α-crystal form by triturating a suspension of the latter in a polar solvent, especially an alcoholic solvent, such as methanol. The β-crystal form could be also obtained directly from the free base by treating a suspension of 4-(4-methylpiperazin-1-ylmethyl)-N-[4-methyl-3-[(4-pyridin-3-yl)pyrimidin-2-yloamino]phenyl]benzamide with methanesulfonic acid in methanol, concentrating the obtained solution and inoculating it with seeds of the β-crystal form.

In WO 99/03854, a general observation was made that the α-crystal form of the methanesulfonic acid addition salt of Imatinib could be obtained, e.g., by precipitating out the salt from its solution in a solvent other than alcohol, such as methanol, and without adding any seeds of the β-crystal form. The method of preparing the α-crystal form, disclosed in Example 1 of WO 99/03854 is as follows:

(1) a suspension of the free base in ethanol is treated with methanesulfonic acid and the solution of the obtained salt is refluxed for 20 min.;

(2) the solution obtained as above is concentrated to a half of its initial volume and the precipitate that has formed is filtered at 25° C., to give the filtration product A;

(3) the filtrate is evaporated to dryness, the filtration product A is then added to the residue followed by appropriate volume of ethanol and water and the mixture is refluxed until completely dissolved;

(4) after cooling the solution slowly down to 25° C., the α-crystal form is isolated by filtration.

However, failed attempts to reproduce Example 1 of WO 99/03854 by Inventors of the present invention have proven that the disclosure of WO 99/03854 is insufficient for preparing the α-crystal form selectively and in a reproducible manner.

On repeating the procedure of the Example 1 with the use of absolute ethyl alcohol (i.e., ethanol containing 0.1% (m/v) of water), Inventors of the present invention have found that the combined filter material A and the residue after evaporating the mother liquor does not completely dissolve in the specified volume of water and ethanol. Despite filtering undissolved crystals and cooling down the reaction mixture to room temperature results in readily crystals formation, comparison of their X-ray powder diffraction pattern with the data provided in WO 99/03854 evidences the formation of β-crystal form. On the other hand, in case of using ethanol containing 4.8% (m/v) of water, the solution concentrated to a half of its volume does not crystallize easily and the final solution of the salt does not crystallize without inoculation with the proper crystal form even after 36 hours after it has been cooled down to about 16° C.

Furthermore, one drawback associated with the process for preparing the α-crystal form, disclosed in the International Publication WO 99/03854, is that it requires several unit operations, such as isolation of crude methanesulfonate crystals from the reaction mixture, evaporating ethanol from the reaction mixture and re-suspending the methanesulfonate salt in the same solvent.

Moreover, Inventors of the present invention have found that without inoculating the reaction mixture with a proper crystal form, crystallization of the methanesulfonic acid addition salt of 4-(4-methylpiperazin-1-ylmethyl)-N-[4-methyl-3-[4-pyridin-3-yl)pyrimidin-2-ylamino]phenyl]benzamide has a random nature, i.e., either the α-crystal form, the β-crystal form or mixtures thereof are obtained randomly without regard to the reaction conditions.

Therefore, it has been necessary to find a selective and reproducible method of preparing the α-crystal form of the methanesulfonic acid addition salt of 4-(4-methylpiperazin-1-ylmethyl)-N-[4-methyl-3-[4-pyridin-3-yl)pyrimidin-2-ylamino]phenyl]benzamide, a method which would be suitable for use as a one-pot reaction.

The problem of the non-selectivity and non-reproducibility of the prior art methods has been solved by a process disclosed in the Polish Patent Application No. P-366885 filed Apr. 2, 2004, in which the reaction of equimolar amounts of methanesulfonic acid and 4-(4-methylpiperazin-1-ylmethyl)-N-[4-methyl-3-(4-pyridin-3-yl)pyrimidin-2-ylamino) phenyl]benzamide is carried out in ethyl alcohol or in a mixture of ethyl alcohol with another $C_1$-$C_4$ aliphatic alcohol; then an ester of a carboxylic acid and $C_1$-$C_4$ aliphatic alcohol is added to the reaction mixture, the reaction mixture is cooled down to the internal temperature A, seeded with the crystals of the α-crystal form and the resulting reaction mixture is left with stirring at internal temperature B for the time necessary for crystallization of the α-crystal form.

Although the method allows for obtaining the pure α-crystal form, it requires using two different solvents, the second of which (an ester of a carboxylic acid and $C_1$-$C_4$ aliphatic alcohol) causes precipitation of the acid addition salt from the reaction mixture. Furthermore, the method requires inoculating the reaction mixture with the seeds of the α-crystal form and the yield of crystallization hardly exceeds 80%.

BRIEF DESCRIPTION OF THE INVENTION

The present invention is based upon the experimental finding that in some cases, when certain solvents or mixtures thereof are used, the obtained α-crystal or β-crystal forms of Imatinib methanesulfonate or their mixture additionally contains morphologically different, previously-unidentified crystals. Dissimilarity of the isolated crystals and the known crystalline forms of Imatinib methanesulfonate has been confirmed by the X-ray structure analysis and the IR spectrum.

Analysis of the isolated crystals by the proton magnetic resonance (NMR) method has demonstrated that they are the acid addition salt of 4-(4-methylpiperazin-1-ylmethyl)-N-[4-methyl-3-[4-pyridin-3-yl)pyrimidin-2-ylamino]phenyl]benzamide with two molecules of methanesulfonic acid, i.e. Imatinib dimethanesulfonate, hereinafter referred to as Imatinib dimesylate.

The discovery of a simultaneous formation of the different crystalline forms of Imatinib monomethanesulfonate and Imatinib dimethanesulfonate, depending upon crystallization conditions, has allowed for developing a more selective method of preparing the α-crystal form of the methanesulfonic acid addition salt of 4-(4-methylpiperazin-1-ylmethyl)-N-[4-methyl-3-[(4-pyridin-3-yl)pyrimidin-2-ylamino]phenyl]benzamide, hereinafter referred to as Imatinib monomesylate.

It was found that by using not more than 0.99 equivalents of methanesulfonic acid per 1.00 equivalent of 4-(4-methylpiperazin-1-ylmethyl)-N-[4-methyl-3-[(4-pyridin-3-yl)pyrimidin-2-ylamino]phenyl]benzamide in the addition reaction allows for obtaining the α-crystal form of Imatinib monomesylate that is essentially free of detectable amounts of Imatinib monomesylate β-crystal form as well as of any Imatinib dimesylate crystalline forms.

Unexpectedly, it has been found also that by restricting the stoichiometric ratio of the reactants it is possible to extend possibility of obtaining the essentially pure α-crystal form of Imatinib monomesylate, in particular to extend the range of usable solvents or their mixtures of a definite composition. However, in some cases, e.g. in case of using a mixture of ethyl alcohol and methyl-tert-butyl ether, formation of Imatinib dimesylate could not be avoided. It seems that in case of certain solvents, the equilibrium between Imatinib free base, Imatinib monomesylate and Imatinib dimesylate is attained, despite using less than 1.00 equivalents of methanesulfonic acid per 1.00 equivalent of Imatinib:

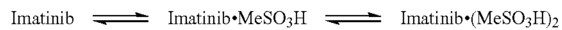

Therefore, a process has been developed that under certain conditions allows for eliminating the need of seeding the crystallization mixture with α-crystal form, by combining the use of the reagents in the stoichiometric ratio of less than 1.00:0.99 with the use of appropriate solvents. Under these conditions, the addition of a precipitating solvent, such as an ester-type solvent, is also not necessary.

The process of the invention for the preparation of an acid addition salt of methanesulfonic acid of 4-(4-methylpiperazin-1-ylmethyl)-N-[4-methyl-3-[(4-pyridin-3-yl)pyrimidin-2-ylamino]phenyl]benzamide in the α-crystal form comprises:

a) carrying out the acid addition reaction of methanesulfonic acid and 4-(4-methylpiperazin-1-ylmethyl)-N-[4-methyl-3-[(4-pyridin-3-yl)pyrimidin-2-ylamino) phenyl]benzamide in a solvent selected from the group consisting of $C_2$-$C_6$ aliphatic alcohols or the mixtures thereof, optionally with the addition of another $C_1$-$C_4$ aliphatic alcohol;

b) adding, if necessary, a solvent selected from the group consisting of esters of lower carboxylic acids and $C_1$-$C_4$ aliphatic alcohols;

c) optionally inoculating the reaction mixture with the α-crystal form;

d) stirring the reaction mixture for the time necessary for crystallization of the α-crystal form; and e) isolating the α-crystal form from the reaction mixture.

In preferred embodiments of the invention, the acid addition reaction is carried out using not more than 0.99 equivalents, and especially from 0.95 to 0.99 equivalents of methanesulfonic acid, per 1.00 equivalent of 4-(4-methylpiperazin-1-ylmethyl)-N-[4-methyl-3-[(4-pyridin-3-yl)pyrimidin-2-ylamino]phenyl]benzamide.

Solvents, suitable for the acid addition reaction and crystallization are those selected from the group comprising n-propyl alcohol, isopropyl alcohol, n-butyl alcohol, tert-butyl alcohol and the mixtures thereof, particularly the mixtures containing ethyl alcohol.

In one variant of this embodiment of the invention, the acid addition reaction is carried out in the mixture of solvents consisting of from 0% to about 50% of ethyl alcohol and from 50% to 100% of n-propyl alcohol (v/v).

In another variant of this embodiment of the invention, the acid addition reaction is carried out in the mixture of solvents consisting of from 0 to about 50% of ethyl alcohol and from 50% to 100% of isopropyl alcohol (v/v).

In still another variant of this embodiment of the invention, the acid addition reaction is carried out in the mixture of solvents containing from 0% to about 50% of ethyl alcohol and from 50% to 100% of n-butyl alcohol (v/v).

In still another variant of this embodiment of the invention, the addition reaction is carried out in the mixture containing from 0% to about 50% of ethyl alcohol and from 50% to 100% of tert-butyl alcohol (v/v).

Appropriate selectivity of crystallization could be attained also by using only one alcohol, preferably n-propyl alcohol, isopropyl alcohol, n-butyl alcohol or tert-butyl alcohol.

Generally, from 15 to 50 volume parts of an alcohol or a mixture of alcohols are used in the addition reaction per 1 weight part of Imatinib base, depending on the used solvent system. The solvent can be introduced in one portion at the beginning of the acid addition reaction or in parts during its course.

In the second embodiment of the invention, in the acid addition reaction the equimolar amounts of the reagents are used. In this case, the necessary condition of the selective crystallization of α-crystal form of Imatinib monomesylate is, upon the completion of the acid addition reaction, adding to the reaction mixture of the ester of lower carboxylic acid and $C_1$-$C_4$ aliphatic alcohol (ester-type solvent). The preferred ester-type solvents could be alkyl esters of formic acid, acetic acid and propionic acid, especially ethyl acetate. The advantageous effect of crystallization is also gained with the addition of isopropyl acetate. The volume of the ester added is at least equal to the volume of alcoholic solvents used.

As has been mentioned above, in the preferred embodiment of the invention the acid addition reaction is carried out using from 0.95 to 0.99 equivalents of methanesulfonic acid per 1.00 equivalent of 4-(4-methylpiperazin-1-ylmethyl)-N-[4-methyl-3-[4-pyridin-3-yl)pyrimidin-2-ylamino]phenyl] benzamide.

The reaction mixture is stirred while maintaining internal temperature of the reaction mixture within the range from room temperature to the boiling temperature of the solution. After addition of the calculated amount of methanesulfonic acid to the suspension of Imatinib base in the selected solvent, one can optionally add an additional amount of the same or another solvent.

The addition of an ester-type solvent in this embodiment is not necessary but it increases the yield of the α-crystal form of Imatinib monomesylate and allows for reducing the volume of the solvent used for suspending Imatinib base. Thus, the method disclosed in the Polish Patent Application No. P-366,885 has now been improved by applying the above-provided preferred ratio of reagents. The effect is evidenced in the Examples 8-11 hereby incorporated in the present application.

Crystallization can be initiated by inoculating the reaction mixture with crystal seeds of α-crystal form of Imatinib monomesylate. However, in many cases inoculation is not necessary because the solvent system and the molar ratio of reagents that have been used are favorable for spontaneous crystallization of the acid addition salt of methanesulfonic acid and 4-(4-methylpiperazin-1-ylmethyl)-N-[4-methyl-3-[4-pyridin-3-yl)pyrimidin-2-ylamino]phenyl]benzamide into the α-crystal form.

After completion of crystallization, the reaction mixture is cooled down and then left with continuous stirring for the time necessary for crystallization of the α-crystal form, i.e., usually for 3-5 hours. The crystalline solid is isolated in a way well-known to those skilled in the art, washed, e.g., with ethyl acetate and dried at first at room temperature in the air and then at room temperature or at elevated temperatures, e.g., about 60° C., under reduced pressure.

The process according to the invention is the selective and reproducible method for preparing an essentially pure α-crystal form of the acid addition salt of methanesulfonic acid and 4-(4-methylpiperazin-1-ylmethyl)-N-[4-methyl-3-[4-pyridin-3-yl)pyrimidin-2-ylamino]phenyl]benzamide.

BRIEF DESCRIPTION OF THE DRAWINGS

FIG. 1 presents a comparison of IR spectra of α- and β-crystal forms of Imatinib monomesylate;

FIG. 2 presents a comparison of DSC curves of α- and β-crystal forms of Imatinib monomesylate;

FIG. 3 presents XRPD pattern of the α-crystal form of Imatinib monomesylate;

FIG. 4 presents XRPD pattern of the β-crystal form of Imatinib monomesylate;

FIG. 5 presents the DSC curve of the crystalline Form I of Imatinib dimesylate;

FIG. 6 presents the DSC curve of the crystalline Form II of Imatinib dimesylate;

FIG. 7 presents the DSC curve of the mixture of crystalline Form I and Form II of Imatinib dimesylate (obtained directly from a crystallization experiment);

FIG. 8 presents a characteristic XRPD pattern of crystalline Form I of Imatinib dimesylate;

FIG. 9 presents a characteristic XRPD pattern of crystalline Form II of Imatinib dimesylate;

FIG. 10 presents a characteristic XRPD pattern of the mixture of crystalline Form I and Form II of Imatinib dimesylate;

FIG. 11 presents the IR spectrum of the crystalline Form I of Imatinib dimesylate;

FIG. 12 presents the IR spectrum of the crystalline Form II of Imatinib dimesylate; and FIG. 13 presents the IR spectrum of the mixture of the crystalline Form I and Form II of Imatinib dimesylate.

DETAILED DESCRIPTION OF THE INVENTION

For the purposes of this invention, the term "essentially pure α-crystal form of Imatinib monomesylate" is to be understood as the α-crystal form of the methanesulfonic acid addition salt of methanesulfonic acid and 4-(4-methylpiperazin-1-ylmethyl)-N-[4-methyl-3-[4-pyridin-3-yl)pyrimidin-2-ylamino]phenyl]benzamide, that contains no admixtures of other crystalline forms of Imatinib monomesylate or any other crystalline solids in amounts detectable by the conventionally used analytical methods, i.e. the form that contains less than 2%, preferably less than 1% by weight of the β-crystal form of Imatinib monomesylate or any other crystalline solids.

The crystalline form of the acid addition salt of methanesulfonic acid and 4-(4-methylpiperazin-1-ylmethyl)-N-[4-methyl-3-[4-pyridin-3-yl)pyrimidin-2-ylamino]phenyl]benzamide, obtained by the method according to the invention, has been analyzed by infra-red (IR) spectroscopy, X-ray powder diffraction (XRPD) and differential scanning calorimetry (DSC) and the obtained results were compared to data for the reference β-crystal form, obtained by the method described in WO 99/03854, Example 1, and to analytical data for both forms provided in the publication of the aforementioned patent application.

The IR spectrum of the α-crystal form, measured using a KBr pellets technique, is essentially different from that of the β-crystal form within the whole range of the spectrum (4,000-400 $cm^{-1}$), as is shown in Table 1.

TABLE 1

FT-IR spectra (KBr pellets): comparison of characteristic bands for the α- and β-crystal forms of Imatinib monomesylate

| α-crystal form | | β-crystal form | |
|---|---|---|---|
| ν, $cm^{-1}$ | Intensity* | ν, $cm^{-1}$ | Intensity* |
| 3257 | m | 3336 | m |
| 3033-3010 | m | 3006-2946 | m |
| 2824-2782 | m | 2801-2758 | m |
| 2706-2492 | m-w | — | |
| 1660 | s | 1656 | s |
| | | 1596 | s |
| 1572 | s | 1574 | s |
| 1527 | s | 1534 | s |
| | | 1482 | s |
| 1447 | s | | |
| 1321 | m | 1310 | m |
| 1221 | s | 1224 | s |
| 1161 | s | 1168 | s |
| 1037 | s | 1037 | s |
| 807 | m | 815 | m |
| 772 | m | 803 | m |
| 749 | m | 765 | m |
| 555 | m | 751 | m |
| | | 549 | m |
| | | 521 | m |

*s = strong, m = moderate, w = weak

The comparison of the IR spectra of the α-crystal form obtained by the method according to the invention and the reference β-crystal form of Imatinib monomesylate within the whole range of the spectrum is presented on FIG. 1

FIG. 2 presents a comparison of DSC curves of the α- and β-crystal forms of Imatinib monomesylate. Endothermic peaks, characteristic for the melting process of the substance are visible on the curves of the α- and β-crystal forms. Compared to those of the α-crystal form, the melting point of the β-crystal form is lower, and corresponding melting enthalpy is larger. The melting points and enthalpies of both crystalline forms are shown also in Table 2. The melting points have been determined by two methods: (i) as the "extrapolated peak" i.e. the intersection point of tangents to the peak curve and (ii) as "the onset", i.e., the intersection point of tangents to the baseline and to the rising line of the peak.

TABLE 2

DSC: Comparison of the melting points and melting enthalpies of the α- and β-crystal forms of Imatinib monomesylate

| | Form α | Form β |
|---|---|---|
| Melting point, ° C. (by peak extrapolation) | 224.3 | 216.5 |
| Melting point, ° C. (by onset) | 223.7 | 214.7 |
| Melting enthalpy, J/g | 108 | 127 |

FIGS. 3 and 4 represent characteristic X-ray powder diffraction patterns of the α- and β-crystal forms of Imatinib monomesylate, where intensity of the relative diffraction peaks of CuKα radiation, and refraction angles 2θ are shown as a function of interplanar distances d, at the refraction angles 2θ from 3° to 40°, scanning rate 0.5 deg/min and counting accuracy of 0.03 deg. The comparison of positions and intensities of main diffraction peaks (of relative intensity over 20% and some weaker peaks suitable for identifying the particular crystalline form) for the α- and β-crystal forms is presented in Tables 3 and 4.

TABLE 3

X-ray powder diffraction patterns of the α-crystal form of Imatinib monomesylate (main diffraction peaks)

| No. of the peak | d (Å) | 2θ (°) | $I/I_0$ (%) |
|---|---|---|---|
| 1 | **17.89** | **4.9** | **10.4** |
| 2 | 8.41 | 10.5 | 53.6 |
| 3 | 5.93 | 14.9 | 37.1 |
| 4 | 5.36 | 16.5 | 26.3 |
| 5 | 5.00 | 17.7 | 51.9 |
| 6 | 4.89 | 18.1 | 64.6 |
| 7 | **4.75** | **18.6** | **100.0** |
| 8 | **4.64** | **19.1** | **72.2** |
| 9 | 4.17 | 21.3 | 61.5 |
| 10 | 4.10 | 21.6 | 73.8 |
| 11 | 3.92 | 22.7 | 23.1 |
| 12 | **3.83** | **23.2** | **32.3** |
| 13 | 3.74 | 23.8 | 29.2 |
| 14 | 3.57 | 24.9 | 76.1 |
| 15 | 3.25 | 27.4 | 22.0 |
| 16 | 3.18 | 28.0 | 21.7 |
| 17 | **3.12** | **28.6** | **72.4** |

TABLE 4

X-ray powder diffraction patterns of the β-crystal form of Imatinib monomesylate (main diffraction peaks)

| No. of the peak | d (Å) | 2θ (°) | $I/I_0$ (%) |
|---|---|---|---|
| 1 | **15.28** | **5.8** | **8.2** |
| 2 | **10.55** | **8.4** | **4.5** |
| 3 | **9.12** | **9.7** | **19.1** |
| 4 | 6.37 | 13.9 | 30.8 |
| 5 | **5.09** | **17.4** | **59.3** |
| 6 | 4.89 | 18.1 | 66.6 |
| 7 | 4.70 | 18.9 | 21.2 |
| 8 | **4.45** | **19.9** | **55.8** |
| 9 | **4.32** | **20.5** | **100.0** |
| 10 | 4.22 | 21.0 | 75.3 |
| 11 | 4.03 | 22.0 | 65.4 |
| 12 | 3.92 | 22.7 | 34.8 |
| 13 | 3.75 | 23.7 | 32.8 |
| 14 | 3.52 | 25.3 | 20.9 |
| 15 | 3.33 | 26.8 | 25.0 |
| 16 | 3.01 | 29.7 | 31.9 |
| 17 | 2.90 | 30.8 | 25.6 |

In Tables 3 and 4, the characteristic peaks that could be suitable for identifying both forms in their mixtures and for determining their crystalline purity, are marked with bold numbers. The peaks, characteristic for the α-crystal form, are observed at the 2θ angles of about: 4.9; 18.6; 19.1; 23.2 and 28.6°, and those for the β-crystal form at the 2θ angles of about: 5.8; 8.4; 9.7; 17.4; 19.9 and 20.5°.

Analysis of the data obtained by X-ray powder diffraction, IR and DSC shows that the method according to the invention provides the α-crystal form of Imatinib monomesylate that is essentially free of any admixtures of the β-crystal form or any other crystalline forms.

As mentioned above, crystallization of the α-crystal form obtained in the addition reaction using equimolar amounts of methanesulfonic acid and 4-(4-methylpiperazin-1-ylmethyl)-N-[4-methyl-3-[(4-pyridin-3-yl)pirimidin-2-ylamino) phenyl]benzamide in certain solvents is very often accompanied by formation of a crystalline impurity. This has been identified by Inventors as Imatinib dimesylate on the base of proton magnetic nuclear resonance ($^1$H NMR (DMSO-$d_6$), with shifts δ (ppm): 10.28 (1H, s, NH), 9.38 (1H, d, J=1.8 Hz), 9.07 (1H, s, NH), 8.81 (1H, dd, J=5.0 i 1.4 Hz), 8.73 (1H, dt, J=8.1 i 1.8 Hz), 8.57 (1H, d, J=5.1 Hz), 8.14 (1H, d, J=1.8 Hz), 8.05 (2H, d, J=8.2 Hz), 7.74 (1H, dd, J=8.0 i 5.1 Hz), 7.63 (2H, d, J=8.1 Hz), 7.51 (1H, dd, J=8.2 i 2.1 Hz), 7.50 (1H, d, J=5.1 Hz), 7.24 (1H, d, J=8.5 Hz), 4.17 (2H, s), 2.9-3.7 (8H, br m), 2.87 (3H, s, N—$CH_3$), 2.45 (6H, s, 2×$CH_3$, 2×$MeSO_3H$), 2.25 (3H, s, Ar—$CH_3$).

Imatinib dimesylate is thus formed in the reaction of 4-(4-methylpiperazin-1-ylmethyl)-N-[4-methyl-3-[(4-pyridin-3-yl)pyrimidin-2-ylamino)phenyl]benzamide with two equivalents of methanesulfonic acid.

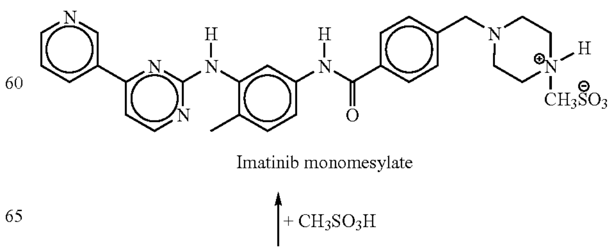

Imatinib monomesylate

+ $CH_3SO_3H$

-continued

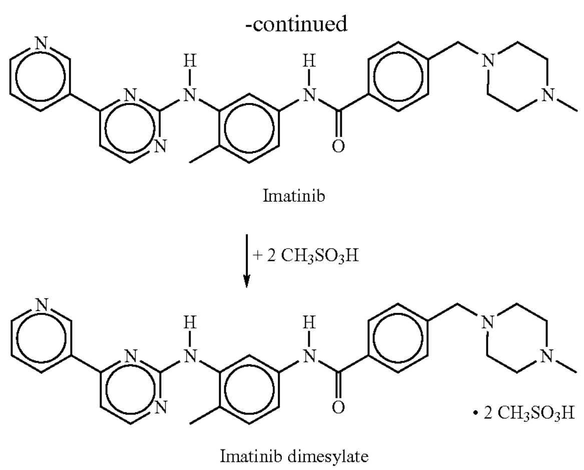

Imatinib dimesylate

Inventors have succeeded in isolating dimethanesulfonic acid addition salt of 4-(4-methylpiperazin-1-ylmethyl)-N-[4-methyl-3-[(4-pyridin-3-yl)pirimidin-2-ylamino)phenyl]benzamide (Imatinib dimesylate) in its crystalline form as an impurity of one of the crystalline forms of Imatinib monomesylate as well as determining its physicochemical properties. The compound was then synthesized which has allowed for proving the existence of its two polymorphs.

Another aspect of the invention is therefore a novel methanesulfonic acid addition salt of 4-(4-methylpiperazin-1-ylmethyl)-N-[4-methyl-3-[(4-pyridin-3-yl)pyrimidin-2-ylamino)phenyl]benzamide that comprises two molecules of the acid per one molecule of Imatinib base, i.e. Imatinib dimesylate.

Imatinib dimesylate crystallizes in two distinct crystalline forms, hereinafter referred to as the Form I and Form II, depending on the solvents used for crystallization and crystallization conditions (with, or without inoculating with the crystal seeds). Under certain conditions, it crystallizes as a mixture of both polymorphs in the weight ratio of approximately 1:1.

The crystalline Forms I and II of Imatinib dimesylate and their mixture can be easily identified and distinguished from each other or from Imatinib monomesylate polymorphs by differential scanning calorimetry (DSC), infra-red absorption spectrum with Fourier transformation (FTIR) and X-ray powder diffractometry (XRPD).

Characteristic endothermic peaks, corresponding to the melting of the substances are visible on the DSC curves of the crystalline Forms I and II of Imatinib dimesylate. The melting point of the Form I is higher than that of the Form II while melting enthalpies are comparable. Two peaks that reflect melting of both forms are visible on the DSC curve of the crystalline mixture. Melting temperatures and enthalpies of the mixture of both forms are presented in Table 5.

TABLE 5

DSC: Comparison of melting temperatures and enthalpies of the crystalline Forms I and II of Imatinib dimesylate and their mixture

| | Form I | Form II | Mixture of Form I and Form II (1:1) |
|---|---|---|---|
| Melting point, ° C. (by peak extrapolation) | 227.2 | 211.0 | 208.8<br>222.2 |
| Melting point, ° C. (by onset) | 225.3 | 205.6 | 202.0<br>216.6 |
| Melting enthalpy, J/g | 100.7 | 103.5 | — |

FIG. 5 shows the characteristic XRPD pattern of Form I of Imatinib dimesylate, FIG. 6 shows the characteristic XRPD pattern of Form II of the compounds and FIG. 7 shows the characteristic XRPD pattern of the crystalline mixture (1:1) of both forms.

Positions and intensities of diffraction peaks of the crystalline Form I and Form II of Imatinib dimesylate and of their mixture are presented in Tables 6, 7 and 8 (the peaks of intensity over 20% are marked with bold figures).

TABLE 6

X-ray powder diffraction data of Form I of Imatinib dimesylate

| d [Å] | 2θ [°] | $I/I_0$ [%] |
|---|---|---|
| 17.71 | 4.98 | 2.1 |
| 10.52 | 8.47 | 4.2 |
| 9.30 | 9.49 | 3.9 |
| 8.89 | 9.93 | 17.2 |
| 8.38 | 10.54 | 1.6 |
| 8.06 | 10.99 | 2.7 |
| 7.04 | 12.56 | 3.4 |
| 6.75 | 13.09 | 6.3 |
| 6.36 | 13.91 | 1.8 |
| 5.92 | 14.94 | 8.8 |
| 5.56 | 15.91 | 5.2 |
| 5.41 | 16.35 | 18.9 |
| **5.22** | **16.94** | **27.4** |
| 4.94 | 17.93 | 7.7 |
| **4.47** | **19.80** | **100.0** |
| **4.41** | **20.08** | **41.7** |
| **4.32** | **20.51** | **32.2** |
| **4.17** | **21.28** | **20.2** |
| **4.10** | **21.65** | **27.2** |
| **4.04** | **21.98** | **30.0** |
| **3.91** | **22.70** | **43.0** |
| **3.85** | **23.07** | **29.3** |
| 3.62 | 24.50 | 17.8 |
| 3.57 | 24.90 | 13.4 |
| 3.39 | 26.22 | 17.9 |
| 3.26 | 27.28 | 14.7 |
| 2.78 | 32.09 | 5.5 |

TABLE 7

X-ray powder diffraction data of Form II of Imatinib dimesylate

| d [Å] | 2θ [°] | $I/I_0$ [%] |
|---|---|---|
| 8.89 | 9.93 | 13.6 |
| 6.19 | 14.28 | 7.7 |
| 6.02 | 14.68 | 15.0 |
| 5.68 | 15.57 | 15.7 |
| 5.50 | 16.08 | 11.3 |
| **5.14** | **17.23** | **22.7** |
| **5.02** | **17.62** | **81.4** |
| **4.73** | **18.72** | **100.0** |
| **4.45** | **19.90** | **39.1** |
| **4.38** | **20.23** | **28.3** |
| **4.17** | **21.25** | **51.0** |
| **4.11** | **21.59** | **84.6** |

TABLE 7-continued

X-ray powder diffraction data of Form II of Imatinib dimesylate

| d [Å] | 2θ [°] | $I/I_0$ [%] |
|---|---|---|
| **4.02** | **22.05** | **48.0** |
| **3.95** | **22.44** | **41.3** |
| **3.80** | **23.38** | **66.3** |
| **3.75** | **23.68** | **40.9** |
| **3.63** | **24.48** | **30.0** |
| **3.50** | **25.41** | **28.7** |
| **3.41** | **26.10** | **44.5** |
| **3.14** | **28.39** | **37.5** |
| 2.79 | 32.02 | 13.9 |
| 2.68 | 33.38 | 12.5 |

TABLE 8

X-ray powder diffraction data of the mixture (1:1) of Form I and Form II of Imatinib dimesylate

| d [Å] | 2θ [°] | $I/I_0$ [%] |
|---|---|---|
| 10.41 | 8.48 | 4.0 |
| 9.31 | 9.48 | 4.5 |
| 8.90 | 9.92 | 17.5 |
| 8.39 | 10.53 | 2.2 |
| 8.04 | 10.99 | 2.3 |
| 5.91 | 14.95 | 9.7 |
| 5.68 | 15.58 | 6.0 |
| 5.41 | 16.34 | 18.2 |
| **5.23** | **16.91** | **27.2** |
| **5.03** | **17.60** | **28.5** |
| **4.74** | **18.69** | **34.3** |
| **4.48** | **19.78** | **100.0** |
| **4.32** | **20.50** | **33.8** |
| **4.10** | **21.60** | **51.9** |
| **4.03** | **22.00** | **42.6** |
| **3.91** | **22.70** | **50.3** |
| **3.85** | **23.07** | **34.9** |
| **3.63** | **24.49** | **26.4** |
| 3.50 | 25.39 | 17.0 |
| **3.40** | **26.13** | **26.2** |
| **3.26** | **27.25** | **24.6** |
| 2.78 | 32.09 | 9.5 |

As shown in Table 9, the IR spectrum of Imatinib dimesylate Form I obtained by the KBr pellet technique is noticeably different from that of Form II within the whole range of wavelengths (4,000-400 $cm^{-1}$). Bands, corresponding to both Form I and Form II are clearly visible in the IR spectrum of the mixture of these forms.

TABLE 9

FT-IR spectrum (KBr pellets): Comparison of the characteristic bands, distinguishing the crystalline Form I and Form II of Imatinib dimesylate and their mixture

| Form I | | Form II | | Mixture of Form I and Form II | |
|---|---|---|---|---|---|
| v, $cm^{-1}$ | Intensity* | v, $cm^{-1}$ | Intensity* | v, $cm^{-1}$ | Intensity* |
| 3435 | m-w (broadband) | 3435 | m. | 3436 | m. |
| 3276 | m | 3237 | m-w | 3275 | m. |
| 3008 | m | 3096 | m-w | 3008 | m. |
| 2483 | m (broad band) | 3007 | m. | 2484 | m (broad band) |
| | | 2468 | m (broad band) | | |
| 1647 | s | 1666 | m-s | 1666 | |
| | | | | 1647 | m. |
| | | 1617 | m. | | |

TABLE 9-continued

FT-IR spectrum (KBr pellets): Comparison of the characteristic bands, distinguishing the crystalline Form I and Form II of Imatinib dimesylate and their mixture

| Form I | | Form II | | Mixture of Form I and Form II | |
|---|---|---|---|---|---|
| v, $cm^{-1}$ | Intensity* | v, $cm^{-1}$ | Intensity* | v, $cm^{-1}$ | Intensity* |
| | | 1603 | m. | | s |
| 1586 | s | 1576 | | 1577 | |
| 1577 | m | | s | | w |
| 1554 | s | | | 1554 | s |
| 1537 | | 1537 | m. | 1537 | |
| | | 1529 | s | | |
| | | | m. | | w |
| | s | 1493 | m. | 1495 | s |
| 1454 | m | 1453 | m. | 1453 | m. |
| 1422 | | 1437 | m-w | 1422 | m. |
| | | 1397 | m-w | 1398 | m. |
| | | 1372 | s | 1373 | |
| 1325 | m | 1337 | s | 1336 | m. |
| 1311 | | 1304 | s | 1311 | |
| 1295 | s | 1283 | m. | 1297 | s |
| 1224 | s | 1225 | w | 1224 | s |
| 1149 | m | 1149 | | 1150 | s |
| 1039 | m-w | 1026 | m. | 1039 | m. |
| 952 | | 945 | | 948 | w |
| | | 910 | m. | 911 | w |
| 892 | m-w | | m. | 892 | m. |
| 870 | | 865 | m-w | 866 | |
| 852 | m | | m. | | m. |
| 798 | m | 806 | w | 806 | m. |
| 772 | | 774 | m. | 773 | |
| 706 | | 710 | | 708 | |
| 691 | | 666 | | 691 | m-w |
| 674 | m-w | 642 | m. | 667 | |
| 647 | | 619 | | 647 | |
| 611 | | 614 | w | 615 | |
| 583 | s | | | | m-s |
| 553 | m | 552 | | 553 | m |
| 532 | | 538 | | 536 | |
| 524 | w | 524 | | 524 | w |
| 478 | | 452 | | 454 | |
| 459 | | 431 | | 429 | |
| 427 | | | | | |

*Band intensity: w—weak, m—moderate, s—strong

Yet another aspect of the invention is the crystalline Form I of the dimethanesulfonic acid addition salt 4-(4-methylpiperazin-1-ylmethyl)-N-[4-methyl-3-[(4-pyridin-3-yl)pyrimidin-2-ylamino)phenyl]benzamide (Form I of Imatinib dimesylate).

The crystalline Form I of Imatinib dimesylate is characterized by the peaks of intensity over 20% at 2θ angles in the X-ray powder diffraction diagram of approximately 16.94, 19.80, 20.08, 20.51, 21.28, 21.65, 21.98, 22.70 and 23.07°.

Form I is formed in such solvent systems as, e.g. ethyl alcohol/tert-butyl-methyl ether, ethyl alcohol/ethyl acetate, isopropyl alcohol.

Another aspect of the invention is the crystalline Form II of the dimethanesulfonic acid addition salt 4-(4-methylpiperazin-1-ylmethyl)-N-[4-methyl-3-[(4-pyridin-3-yl)pyrimidin-2-ylamino)phenyl]benzamide (Form II of Imatinib dimesylate).

The crystalline Form II of Imatinib dimesylate is characterized by the peaks of intensity over 20% at 2θ angles in the X-ray powder diffraction diagram of approximately 17.23, 17.62, 18.72, 19.90, 20.23, 21.25, 21.59, 22.05, 22.44, 23.38, 23.68, 24.48, 25.41, 26.10 and 28.39°.

Form II is formed in such solvent systems as, e.g. ethyl alcohol/acetone, methyl alcohol.

In some cases, Imatinib dimesylate crystallizes as a mixture of the Forms I and II in the weight ratio approximately 1:1 in the same solvents as above, e.g. in ethyl alcohol, ethyl alcohol/ethyl acetate, but without seeding the reaction mixture with crystal seeds.

Yet another aspect of the invention is the mixture of the crystalline Form I and Form II of the dimethanesulfonic acid addition salt 4-(4-methylpiperazin-1-ylmethyl)-N-[4-methyl-3-[(4-pyridin-3-yl)pyrimidin-2-ylamino)phenyl]benzamide in the weight ratio of about 1:1, characterized by the peaks of intensity over 20% at 2θ angles in the X-ray powder diffraction pattern of approximately: 16.91, 17.60, 18.69, 19.78, 20.50, 21.60, 22.00, 22.70, 23.07, 24.49, 26.13 and 27.25°.

4-(4-Methylpiperazin-1-ylmethyl)-N-[4-methyl-3-[(4-pyridin-3-yl)pyrimidin-2-ylamino)phenyl]benzamide dimesylate has advantageous physicochemical properties, it is thermodynamically stable and non-toxic, hence as a pharmaceutically acceptable salt (Handbook of Pharmaceutical Salts, P. H. Stahl, C. G. Wermuth (eds.), Verlag Helvetica Chimica Acta, 2002) it could be used as an active ingredient in pharmaceutical compositions having anti-neoplastic activity.

For therapeutic applications, Imatinib dimesylate is formulated into pharmaceutical compositions containing a therapeutically efficacious amount of the active ingredient in combination with at least one pharmaceutically acceptable carrier and/or diluent.

The pharmaceutical composition according to the invention is administered to a patient in need of such treatment in a suitable pharmaceutical dosage form, by the route appropriate for the dosage form, e.g. orally or parenterally (intravenously, intramuscularly or subcutaneously).

Selection of the dose and dosage regimen depends on the type of disease, age, weight and condition of the patient and they could be determined by a specialist on the basis of known procedures of treatment and prevention of such diseases. Preferred dose of the salt according to the invention can be 100-500 mg, calculated on free 4-(4-methylpiperazin-1-ylmethyl)-N-[4-methyl-3-[(4-pyridin-3-yl)pyrimidin-2-ylamino)phenyl]benzamide. The dose can be administered to the patient once per day or several times per day, separately or in a combination with other medicinal substances. Such substances can be administered concurrently as a single preparation or in different preparations. Alternatively, the preparations could be administered subsequently in the order and time intervals determined by a specialist.

The active ingredient can be formulated in various combinations, well known to those skilled in the art, such as those described, e.g., in Remington's Pharmaceutical Sciences, XVI$^{th}$ ed., Mack Publ. Co., 1980.

The pharmaceutical preparations for oral administration comprise tablets, drageés, powders, granules, pellets or capsules containing solid, pharmaceutically acceptable excipients such as corn starch, lactose, sucrose, sorbitol, talc, mannitol or dicalcium phosphate. The tablets or granules can be coated or otherwise processed in order to obtain a dosage Form providing advantageous, prolonged activity. Numerous substances can be used for preparing such protecting layers comprise various polymeric acids and mixtures thereof, with such substances as shellac, cetyl alcohol or cellulose acetate.

It is reasonable to consider administration of Imatinib dimesylate containing pharmaceutical preparations as the preparations for injection or infusions. Such preparations comprise sterile aqueous, aqueous-organic and non-aqueous solutions, suspensions, dry substances and tablets for preparing solutions or for implantation. Excipients that ensure a uniform distribution of the medicinal substance as the liquid, used for preparing suspensions comprise polysorbates, lecithin, copolymers of polyoxyethylene with polyoxypropylene, peptizing agents such as phosphates, polyphosphates and citrates, water-soluble polymers such as carboxymethylcellulose, methylcellulose, polyvinylpyrrolidone, resins or gelatin. The injectable compositions can contain pharmaceutically acceptable excipients such as pH-adjusting agents and buffers, tonicity modifiers and preservatives. The dry substances are designated for preparation of solutions or suspensions ex tempore by diluting the substances using appropriate solvents.

Experimental Section

DSC analyses were performed using the Mettler Toledo DSC 822 apparatus in 40 μL aluminum crucibles that were initially compressed hermetically and then punctured. The analyses were performed under a stream of nitrogen at the flow rate of 60 mL/min. within the temperature range 30-260° C. at the heating rate of 5° C./min. in the dynamic phase, preceded by an isothermal phase (30° C. for 5 min.) in order to stabilize the oven temperature at the initial measurement value. The melting points have been determined by two methods: (i) as the "extrapolated peak" i.e. the intersection point of tangents to the peak curve and (ii) as "the onset", i.e. the intersection point of tangents to the baseline and to the rising line of the peak.

The X-ray powder diffraction (XRPD) diagrams were obtained using a Mini Flex powder diffractometer supplied by Rigaku. The measurement parameters were as follows:

range of 2θ angle: 3.0-40.0°,

CuK$\alpha_1$ radiation wavelength $\lambda$=1.54056 Å, scanning rate: 0.5° per minute, accuracy $\Delta 2\theta$=0.03°.

Infra-red (IR) spectra were obtained from pellets pressed with KBr using a FT-IR spectrometer Perkin Elmer type BX within the range of 4,000-400 cm$^{-1}$ and resolution of 4 cm$^{-1}$.

The invention is further illustrated by the following, non-limiting examples.

EXAMPLES

A. Imatinib Monomesylate

Example 1

The suspension of 4-(4-methylpiperazin-1-ylmethyl)-N-[4-methyl-3-(4-pyridin-3-yl)pyrimidin-2-ylamino)phenyl]benzamide 3.802 g (0.01 mole) in absolute ethyl alcohol (85 mL) was heated with stirring to 75° C., and thereafter methanesulfonic acid (0.5 mL, 0.01 mole) was slowly added dropwise. The mixture was further heated at 75° C. for 10 min. Ethyl acetate (85 mL) was added dropwise and the mixture was cooled down to 30° C. while being stirred. The seeds of α-crystal form (17 mg) were added and then the mixture was cooled down and stirred at 13 to 20° C. for 4 h. The crystals were filtered off, washed with 40 mL of ethyl acetate and dried. Yield: 2.954 g (65.0%); the product that has been identified as Imatinib mesylate α-crystal form.

Examples 2-7

Imatinib mesylate α-crystal form has been prepared according to the general method described in the Example 1, using Imatinib base: methanosulfonic acid=1:1 (mole/mole), with different crystallization parameters.

TABLE

Crystallization parameters

| No. | Solvent in the addition reaction (mL) | Ester-type solvent (mL) | Temp. A (°) | Temp. B (°) | Crystal-lization time (h) | Yield (g, %) |
|---|---|---|---|---|---|---|
| 1 | ethyl alcohol (85) | ethyl acetate (85) | 30 | 13-20 | 4 | 2.954 65.0% |
| 2 | ethyl alcohol (75) | ethyl acetate (100) | 30 | 15-18 | 3.40 | 2.957 65.1% |
| 3 | ethyl alcohol (85) + water (0, 5) | ethyl acetate (85) | 25 | 17-21 | 3.50 | 2.733 60.1% |
| 4 | ethyl alcohol (85) | isopropyl acetate (85) | 25 | 16-18 | 4.40 | 3.790 83.4% |
| 5 | ethyl alcohol (40) + methyl alcohol (45) | isopropyl acetate (85) | 25 | 16-20 | 4.50 | 2.229 49.1% |
| 6 | ethyl alcohol (65) + isopropyl alcohol (20) | ethyl acetate (85) | 24 | 16-20 | 4.20 | 3.951 87.0% |
| 7 | ethyl alcohol (85) | ethyl acetate (85) | 21 | 20-21 | 5 | 3.168 69.7% |

Example 8

Methanesulfonic acid (0.73 g, ca. 0.99 eq.) was added, with stirring, to a suspension of Imatinib (3.802 g, 0.01 mol) in ethyl alcohol (63 mL) heated previously to 65° C. and the mixture was stirred for 10 min. Ethyl acetate (63 mL) was then added slowly dropwise and the mixture was cooled down to 34° C. while being stirred. The seeds of the α-crystal form (50 mg) were added and then the mixture was cooled down and stirred at room temperature for 4.5 h. The crystals were filtered off, washed with 30 mL of ethyl acetate and dried under reduced pressure at room temperature. Yield: 3.699 g (81.4%) of the product that has been identified as Imatinib monomesylate α-crystal form.

Example 9

Methanesulfonic acid (ca. 0.99 eq.) was added, with stirring to a suspension of Imatinib (39.96 g, 0.08 mol) in the mixture of ethyl alcohol (890 mL) and ethyl acetate (200 mL) heated previously to 65° C. The solution was stirred for 10 min. and then ethyl acetate (690 mL) was added slowly dropwise. The mixture was slowly cooled down to 39° C. while being stirred and then 1.215 g of the seeds of the α-crystal form was added and the mixture was slowly cooled down to 22° C. Next, the mixture was left without stirring at room temperature (ca. 19° C.) for two days. The product was filtered off and washed with 100 mL of ethyl acetate. The crystals were dried under reduced pressure at room temperature. Yield: 44.43 g (93.1%) of the product.

Example 10

Methanesulfonic acid (ca. 0.99 eq.) was added, with stirring to a suspension of Imatinib (10.647 g) in ethyl alcohol (173 mL) heated previously to 65° C. and the mixture was stirred for 5 min. The seeds of the α-crystal form (0.279 g) were added to the solution at approx. 44° C. followed by dropwise addition of isopropyl alcohol (65 mL) and ethyl acetate (238 mL). Stirring at room temperature (approx. 24-25° C.) was continued for 4 hours and then the mixture was left without stirring for 64 h. The product was filtered off and washed with 50 mL of ethyl acetate. The crystals were dried under reduced pressure at room temperature to afford 11.85 g (93.1%) of α-crystal form of Imatinib monomesylate.

Example 11

Methanesulfonic acid (ca. 0.99 eq.) was added, with stirring to a suspension of Imatinib (37.997 g) in ethyl alcohol (620 mL) heated previously to 75° C. The resulting solution was stirred for 15 min. and then isopropyl alcohol (230 mL) and ethyl acetate (750 mL) were added dropwise. The mixture was stirred and slowly cooled down to 31.5° C. and then 0.994 g of the seeds of the α-crystal form were added followed by dropwise addition of ethyl acetate (100 mL). The mixture was further cooled down to 22-23° C. Stirring at that temperature was continued for 4 h. Then the mixture was left without stirring overnight at ca. 20° C. The product was filtered off and washed with 100 mL of ethyl acetate. The crystals were dried under reduced pressure at room temperature to afford 43.814 g (96.5%) of the product.

Example 12

Methanesulfonic acid (ca. 0.99 eq.) was added, with stirring to a suspension of Imatinib (3.802 g) in ethyl alcohol (85 mL) heated previously to 68° C. After 5 min., isopropyl alcohol (85 mL) was added dropwise. The mixture was slowly cooled down with stirring, and 50 mg of the seeds of the α-crystal form was added at ca. 37° C. The mixture was cooled down to 21° C. (in total, the mixture was stirred for approximately 6.5 h since seeding). The mixture was left without stirring overnight at approx. 21° C. The product was filtered off and washed with 25 mL of ethyl acetate. The crystals were dried under reduced pressure at room temperature to afford 4.393 g (96.7%) of the product.

Example 13

Methanesulfonic acid (ca. 0.99 eq.) was added, with stirring to a suspension of Imatinib (39.96 g) in the mixture of ethyl alcohol (890 mL) and isopropyl alcohol (200 mL) heated previously to 65° C. The solution was stirred for 10 min. and then isopropyl alcohol (690 mL) was added slowly dropwise. The mixture was slowly cooled down to 39° C. while being stirred and then 1.118 g of the seeds of the α-crystal form was added and the mixture was slowly cooled down to approx. 22° C. Next, the mixture was left without stirring at room temperature (ca. 20° C.) for two days. The product was filtered off and washed with 100 mL of ethyl acetate. The crystals were dried under reduced pressure at room temperature to afford 46.88 g (98.2%) of the product.

Example 14

Methanesulfonic acid (ca. 0.99 eq.) was added, with stirring to a suspension of Imatinib (78.56 g) in ethyl alcohol (1,100 mL) heated previously to 71° C. The solution was stirred for 10 min at 72-75° C. and then isopropyl alcohol (1,000 mL) was added slowly dropwise to the hot solution. The mixture was slowly cooled down to 45° C. and 1.276 g of the seeds of the α-crystal form was added. After cooling the mixture down to approximately 20° C., it was stirred at this temperature for 3 h. The product was filtered off and washed with 150 mL of ethyl acetate. The crystals were dried under reduced pressure at room temperature to afford 91.12 g (97.1%) of the product.

Example 15

Methanesulfonic acid (ca. 0.99 eq.) was added, with stirring to a suspension of Imatinib (7.604 g) in ethyl alcohol (11 mL) heated previously to 69° C. Isopropyl alcohol (225 mL) was slowly added dropwise to the resulting solution. The mixture was slowly cooled down with stirring, and 100 mg of the seeds of the α-crystal form was added at ca. 38° C. (the solution was slightly turbid). The mixture was cooled down to 21° C. (in total, the mixture was stirred for approximately 6.5 h since seeding). The mixture was left without stirring overnight at approx. 21° C. The product was filtered off and washed with 50 mL of ethyl acetate. The crystals were dried under reduced pressure at room temperature to afford 8.502 g (93.6%) of the product.

Example 16

Methanesulfonic acid (ca. 0.99 eq.) was added, with stirring to a suspension of Imatinib (22.76 g) in ethyl alcohol (180 mL) heated previously to 75° C. Isopropyl alcohol (820 mL) was slowly added dropwise. The mixture was slowly cooled down with stirring, and at ca. 44° C. 0.600 g of the seeds of the α-crystal form was added. The mixture was cooled down to 21° C. (in total, the mixture was stirred for approximately 6.5 h since seeding). The mixture was left without stirring overnight at approx. 21° C. The product was filtered off and washed with 100 mL of ethyl acetate. The crystals were dried under reduced pressure at room temperature to afford 26.721 g (98.3%) of the product.

Example 17

Methanesulfonic acid (ca. 0.99 eq.) was slowly added, with stirring to a suspension of Imatinib (10.00 g) in the mixture of ethyl alcohol (79 mL) and isopropyl alcohol (360 mL) heated previously to 45° C. and then 0.282 g of the seeds of the α-crystal Form was added. The mixture was cooled down to room temperature for 5 h and then left without stirring at room temperature (approx. 21° C.) overnight. The product was filtered off and washed with 80 mL of ethyl acetate. The crystals were dried under reduced pressure at room temperature to afford 11.671 g (97.7%) of the product.

Example 18

Methanesulfonic acid (ca. 0.99 eq.) was added at room temperature (24-24.5° C.), with stirring to a suspension of Imatinib (10.000 g) in the mixture of ethyl alcohol (79 mL) and isopropyl alcohol (360 mL). The resulting mixture was heated to 70° C., at which point almost all crystals have dissolved. Next, the mixture was allowed to cool down to room temperature spontaneously for 3 h 50 min. The mixture was left overnight at room temperature (22° C.) without stirring. The product was filtered off and washed with 80 mL of ethyl acetate. The crystals were dried under reduced pressure at room temperature to afford 11.187 g (93.6%) of the product.

Example 19

Methanesulfonic acid (ca. 0.99 eq.) was added, with stirring to a suspension of Imatinib 22.76 g) in ethyl alcohol (182 mL) heated previously to 76° C. Isopropyl alcohol (250 mL) was added dropwise to the resulting solution and the whole mixture was heated to 70° C. The mixture was slowly cooled down with stirring, and 0.600 g of the seeds of the α-crystal form was added at ca. 44° C. Next, isopropyl alcohol (850 mL) was added dropwise and the mixture was further cooled down to 22° C. Stirring was continued at that temperature for 0.5 h and then the mixture was left without stirring overnight at approx. 22° C. The product was filtered off and washed with 100 mL of isopropyl alcohol and 75 mL of ethyl acetate. The crystals were dried under reduced pressure at room temperature to afford 26.306 g (96.7%) of the product.

Example 20

Methanesulfonic acid (ca. 0.99 eq.) was added, with stirring to a suspension of Imatinib (1.521 g) in isopropyl alcohol (75 mL) heated previously to 65° C. and then the mixture was stirred and maintained at approx. 65-70° C. until the solids dissolved. The mixture was then slowly cooled down with stirring, and 27 mg of the seeds of the α-crystal form was added at 34° C. Next, the mixture was slowly cooled down to room temperature and stirring was continued for 4.5 h. The product was filtered off and washed with 15 mL of isopropyl alcohol. The crystals were dried under reduced pressure at room temperature to afford 1.761 g (96.9%) of the product.

Example 21

Methanesulfonic acid (ca. 0.99 eq.) was added, with stirring to a suspension of Imatinib (10.88 g) in isopropyl alcohol (536 mL) heated previously to 75° C. The resulting solution was slowly cooled down with stirring, and 0.285 g of the seeds of the α-crystal form was added at ca. 40° C. (slight turbidity). Next, the mixture was cooled down to room temperature (total cooling time 1 h 15 min.). The mixture was left without stirring overnight at approx. 22° C. The product was filtered off and washed with 100 mL of ethyl acetate. The crystals were dried under reduced pressure at room temperature to afford 12.521 g (96.3%) of the product.

Example 22

Methanesulfonic acid (ca. 0.99 eq.) was added, with stirring to a suspension of Imatinib (10.023 g) in isopropyl alcohol (440 mL) heated previously to 65° C. The mixture was then left to cool down to 22.5° C. spontaneously (approx. 7 h). The product was filtered off and washed with 45 mL of isopropyl alcohol. The crystals were dried under reduced pressure at room temperature to afford 11.784 g (98.4%) of the product.

Example 23

Methanesulfonic acid (ca. 0.99 eq.) was added, with stirring to a suspension of Imatinib (5.326 g) in n-propyl alcohol (230 mL) heated previously to 72° C. The mixture was stirred for 5 min. and cooled down. Seeds of the α-crystal form (100 mg) were added at 30° C. The mixture was further cooled down to approx. 21° C. and then stirred at this temperature for 2.5 h. The product was filtered off and washed with 40 mL of ethyl acetate. The crystals were dried under reduced pressure at room temperature.

Example 24

Methanesulfonic acid (ca. 0.99 eq.) was added, with stirring to a suspension of Imatinib (5.325 g) in n-butyl alcohol (230 mL) heated previously to 70° C. The mixture was stirred for 5 min. and cooled down. Seeds of the α-crystal form (105 mg) were added at 38° C. The mixture was further cooled down slowly to approx. 18° C. (within 3.5 h). The product was filtered off and washed with 25 mL of isopropyl alcohol and 30 mL of ethyl acetate. The crystals were dried under reduced pressure at room temperature.

Example 25

Methanesulfonic acid (ca. 0.99 eq.) was added, with stirring to a suspension of Imatinib (5.320 g) in tert-butyl alcohol (230 mL) heated previously to 70° C. The yellow-orange mixture was maintained at 75-80° C. for 1 h, and then cooled down slowly (within 1 h 40 min.) to 27° C. The product was filtered off and washed with 50 mL of ethyl acetate. The crystals were dried under reduced pressure at room temperature.

B. Imatinib Dimesylate

Example 26

Methanesulfonic acid (0.4 mL) was added dropwise, with stirring to a suspension of Imatinib (1.521 g) in absolute ethyl alcohol (20 mL) heated previously to approx. 65° C. tert-Butyl-methyl ether (MTBE) was added slowly dropwise to the warm solution, until it became turbid (6 mL). After 1 h of stirring at room temperature, 5 mL of absolute ethyl alcohol was added and stirring was continued for 4 h. The precipitate was filtered off and washed with 2 mL of absolute ethyl alcohol and 5 mL of MTBE. The product was dried under reduced pressure at room temperature to afford 0.739 g of Form I of Imatinib dimesylate.

Example 27

Methanesulfonic acid (0.4 mL) was added dropwise, with stirring to a suspension of Imatinib (1.521 g) in absolute ethyl alcohol (20 mL) heated previously to approx. 65° C. tert-Butyl-methyl ether (MTBE) was added slowly dropwise to the warm solution, until it became slightly turbid (4.5 mL) followed by seeds of the crystalline form I. After 0.5 h of stirring at room temperature, 5 mL of absolute ethyl alcohol was added and stirring was continued for 1 h. Next, the mixture was heated to approximately 35° C. and stirred at this temperature for 1 h, and then at room temperature for 2.5 h. The precipitate was filtered off and washed with 10 mL of absolute ethyl alcohol. The product was dried under reduced pressure at room temperature to afford 1.370 g of Form I of Imatinib dimesylate.

Example 28

Methanesulfonic acid (0.4 mL) was added dropwise with stirring to a suspension of Imatinib (1.521 g) in isopropyl alcohol (70 mL) heated previously to approx. 65° C. The mixture was heated to 70° C. and then slowly cooled down. Seeds of the crystalline Form I were added at 65° C. and the cooling was continued. After 3 h of stirring at room temperature the yellow precipitate was filtered off and washed with 10 mL of isopropyl alcohol. The product was dried under reduced pressure at room temperature to afford 1.967 g of Form I of Imatinib dimesylate.

Example 29

Methanesulfonic acid (0.4 mL) was added dropwise, with stirring to a suspension of Imatinib (1.521 g) in absolute ethyl alcohol (20 mL) heated previously to approx. 65° C. 20 mL of ethyl acetate was added slowly dropwise to the warm solution and stirring was continued. The seeds of the Form I were added at 40° C. The mixture was continued at room temperature for approximately 2 h. and the cooling was continued. The product was filtered off and washed with 10 mL of ethyl acetate. The product was dried under reduced pressure at room temperature to afford 1.983 g of Form I of Imatinib dimesylate.

Example 30

Methanesulfonic acid (0.4 mL) was added dropwise, with stirring to a suspension of Imatinib (1.521 g) in absolute ethyl alcohol (20 mL) heated previously to approx. 65° C. The mixture was stirred at this temperature for 10 min. Next, the mixture was cooled down to room temperature. After 0.5 h, 20 mL of acetone was added dropwise and the mixture was stirred at room temperature for 1 h 50 min. Next, another 20 mL of acetone was added dropwise followed by the seeds of the Form I. After 50 min., additional 10 mL of acetone was added dropwise and the mixture was stirred at room temperature for 1 h 20 min. The product was filtered off and washed with 25 ml of acetone and 35 mL of hexane to afford crystals of Form II of Imatinib dimesylate.

Example 31

Methanesulfonic acid (0.4 mL) was added dropwise, with stirring to a suspension of Imatinib (1.521 g) in absolute ethyl alcohol (20 mL) heated previously to approx. 65° C. and the mixture was stirred at this temperature for 10 min. The mixture was then cooled down to room temperature and 40 mL of acetone was added slowly dropwise. Next, the seeds of the crystal Form II were added to the mixture followed by slow dropwise addition of 10 mL of acetone. The mixture was stirred at room temperature for 3 h. The product was filtered off and washed with 20 ml of acetone. The product was dried under reduced pressure at room temperature to afford crystals of Form II of Imatinib dimesylate.

Example 32

A mixture of the products from Examples 5 and 6 (1.551 g) was treated with 25 mL of methyl alcohol and the resulting suspension was stirred at room temperature for 1 h 50 min. Next, the mixture was heated and the resulting solution was slowly cooled down to room temperature. The seeds of the crystalline Form II were added and stirring at room temperature was continued (4 h 40 min. since the mixture was heated). The product was filtered off and washed with a minimal amount of methanol. Next, the product was dried at room temperature under reduced pressure to afford crystals of Form II of Imatinib dimesylate.

Example 33

Methanesulfonic acid (0.4 mL) was added dropwise, with stirring to a suspension of Imatinib (1.521 g) in absolute ethyl alcohol (20 mL) heated previously to approx. 65° C. Ethyl acetate was added dropwise to the warm solution until a slight turbidity was observed (27 mL). Next, the seeds of the crystal Form II were added and the mixture was stirred at room temperature for 4 h. The product was filtered off and washed with 20 ml of ethyl acetate. The product was dried under reduced pressure at room temperature. A crystalline mixture of the Forms I and II of Imatinib dimesylate was obtained (weight ratio about 1:1).

Example 34

Methanesulfonic acid (0.4 mL) was slowly added dropwise to a stirred suspension of Imatinib (1.521 g) in absolute ethyl alcohol (20 mL) at room temperature. The mixture was heated to the boiling point, then 10 mL of absolute ethyl alcohol was added and the mixture was again heated to the boiling point and stirred at this temperature for 3 h and 20 min. The product was filtered off and washed with 15 ml of absolute ethyl alcohol. The product was dried under reduced pressure at room temperature. A crystalline mixture of the Forms I and II of Imatinib dimesylate was obtained (weight ratio about 1:1).

Example 35

Methanesulfonic acid (0.4 mL) was slowly added dropwise to a stirred suspension of Imatinib (1.521 g) in absolute ethyl alcohol (20 mL) previously heated to 70° C. Ethyl acetate (20 mL) was added slowly to the hot solution and stirring was continued at room temperature. After 3.5 h, the precipitate was filtered off and washed with a mixture of anhydrous ethanol and ethyl acetate (1:1, 20 mL). The product was dried under reduced pressure at room temperature. A crystalline mixture of the Forms I and II of Imatinib dimesylate was obtained (weight ratio about 1:1).

What is claimed is:

1. A process for the preparation of the α-crystal form of the methanesulfonic acid addition salt of 4-(4-methylpiperazin-1-ylmethyl)-N-[4-methyl-3-[4-pyridin-3-yl)pyrimidin-2-ylamino]phenyl]benzamide comprising:

a) carrying out an acid addition reaction using not more than 0.99 equivalents of methanesulfonic acid per 1 equivalent of 4-(4-methylpiperazin-1-ylmethyl)-N-[4-methyl-3-[(4-pyridin-3-yl)pyrimidin-2-ylamino)phenyl]benzamide, in a solvent selected from the group consisting of $C_2$-$C_6$ aliphatic alcohols and the mixtures thereof, optionally with the addition of a $C_1$-$C_4$ aliphatic alcohol;

b) optionally adding a solvent selected from the group consisting of esters formed from a $C_1$-$C_4$ aliphatic alcohol and formic acid, acetic acid, or propionic acid;

c) optionally inoculating the reaction mixture with the α-crystal form;

d) stirring the reaction mixture for the time necessary for crystallization of the α-crystal form; and e) isolating the α-crystal form from the reaction mixture, wherein said α-crystal form of the methanesulfonic acid addition salt of 4-(4-methylpiperazin-1-ylmethyl)-N-[4-methyl-3-[(4-pyridin-3-yl)pyrimidin-2-ylamino) phenyl]benzamide isolated from the reaction mixture shows an X-ray powder diffraction pattern that is characterized by having peaks at 2θ angles of approximately: 4.9; 18.6; 19.1; 23.2 and 28.6°.

2. The process according to claim 1 in which the acid addition reaction is carried out using from 0.95 to 0.99 equivalents of methanesulfonic acid per 1 equivalent of 4-(4-methylpiperazin-1-ylmethyl)-N-[4-methyl-3-[(4-pyridin-3-yl)pyrimidin-2-ylamino)phenyl]benzamide.

3. The process according to claim 1, in which the acid addition reaction is carried out in an alcohol selected from the group consisting of n-propyl alcohol, isopropyl alcohol, n-butyl alcohol, tert-butyl alcohol, and the mixtures thereof with ethyl alcohol.

4. The process according to claim 1, in which the acid addition reaction is carried out in a mixture of solvents containing from 0 to 50% of ethyl alcohol and from 50 to 100% of n-propyl alcohol (v/v).

5. The process according to claim 1 in which the acid addition reaction is carried out in the mixture of solvents containing from 0 to 50% of ethyl alcohol and from 50 to 100% of isopropyl alcohol (v/v).

6. The process according to claims 1 in which the acid addition reaction is carried out in a mixture of solvents containing from 0 to 50% of ethyl alcohol and from 50 to 100% of n-butyl alcohol (v/v).

7. The process according to claims 1 in which the acid addition reaction is carried out in a mixture of solvents containing from 0 to 50% of ethyl alcohol and from 50 to 100% of tert-butyl alcohol (v/v).

8. A process for the preparation of the α-crystal form of the methanesulfonic acid addition salt of 4-(4-methylpiperazin-1-ylmethyl)-N-[4-methyl-3-[4-pyridin-3-yl)pyrimidin-2-ylamino]phenyl]benzamide comprising:

a) carrying out an acid addition reaction using 1 equivalent of methanesulfonic acid per 1 equivalent of 4-(4-methylpiperazin-1-ylmethyl)-N-[4-methyl-3-[(4-pyridin-3-yl)pyrimidin-2-ylamino)phenyl]benzamide in the ethyl alcohol, optionally with the addition of a $C_1$-$C_4$ aliphatic alcohol;

b) adding a solvent selected from the group consisting of esters formed from a $C_1$-$C_4$ aliphatic alcohol and formic acid, acetic acid, or propionic acid;

c) inoculating the reaction mixture with the α-crystal form;

d) stirring the reaction mixture for the time necessary for crystallization of the α-crystal form; and e) isolating the α-crystal form from the reaction mixture, wherein said α-crystal form of the methanesulfonic acid addition salt of 4-(4-methylpiperazin-1-ylmethyl)-N-[4-methyl-3-[(4-pyridin-3-yl)pyrimidin-2-ylamino) phenyl]benzamide isolated from the reaction mixture shows an X-ray powder diffraction pattern that is characterized by having peaks at 2θ angles of approximately: 4.9; 18.6; 19.1; 23.2 and 28.6°.

9. The process according to claim 8 wherein said $C_1$-$C_4$ aliphatic alcohol is methyl alcohol or isopropyl alcohol, and the proportion of said $C_1$-$C_4$ aliphatic alcohol to other solvents present in the reaction mixture do not exceed 55% (v/v).

10. The process according to claim 1 in which the acid addition reaction is carried out with stirring while maintaining the internal temperature of the reaction mixture within the range from room temperature to boiling temperature.

11. The process according to claim 1 in which said α-crystal form of the methanesulfonic acid addition salt of 4-(4-methylpiperazin-1-ylmethyl)-N-[4-methyl-3-[(4-pyridin-3-yl)pyrimidin-2-ylamino)phenyl]benzamide isolated from the reaction mixture shows an X-ray powder diffraction pattern that is characterized by having peaks of relative intensity over 20% at 2θ angles of approximately: 4.9, 10.5; 14.9; 16.5; 17.7; 18.1; 18.6; 19.1; 21.3; 21.6; 22.7; 23.2; 23.8; 24.9; 27.4; 28.0 and 28.6°, the relative intensity being determined with respect to the most intense peak by peak height, the peak height expressing a number of counts per second.

12. The process according to claim 2, in which the acid addition reaction is carried out in an alcohol selected from the group comprising n-propyl alcohol, isopropyl alcohol, n-butyl alcohol, tert-butyl alcohol and the mixtures thereof with ethyl alcohol.

13. The process according to claim 2 in which the addition reaction is carried out in the mixture containing from 0 to 50% of ethyl alcohol and from 50 to 100% of n-propyl alcohol (v/v).

14. The process according to claims 2 in which said α-crystal form of the methanesulfonic acid addition salt of 4-(4-methylpiperazin-1-ylmethyl)-N-[4-methyl-3-[(4-pyridin-3-yl)pyrimidin-2-ylamino)phenyl]benzamide isolated from the reaction mixture shows an X-ray powder diffraction pattern that is characterized by having peaks at 2θ angles of approximately 4.9, 10.5; 14.9; 16.5; 17.7; 18.1; 18.6; 19.1; 21.3; 21.6; 22.7; 23.2; 23.8; 24.9; 27.4; 28.0 and 28.6°.

15. The process according to claim 8 in which the acid addition reaction is carried out with stirring while maintaining the internal temperature of the reaction mixture within the range from room temperature to boiling temperature.

16. The process according to claim 8 in which said α-crystal form of the methanesulfonic acid addition salt of 4-(4-methylpiperazin-1-ylmethyl)-N-[4-methyl-3-[(4-pyridin-3-yl)pyrimidin-2-ylamino)phenyl]benzamide isolated from the reaction mixture shows an X-ray powder diffraction pattern that is characterized by having peaks of relative intensity over 20% at 2θ angles of approximately: 4.9, 10.5; 14.9; 16.5; 17.7; 18.1; 18.6; 19.1; 21.3; 21.6; 22.7; 23.2; 23.8; 24.9; 27.4; 28.0 and 28.6°, the relative intensity being determined with respect to the most intense peak by peak height, the peak height expressing a number of counts per second.

17. The process of claim 8 wherein said α-crystal form of the methanesulfonic acid addition salt of 4-(4-methylpiperazin-1-ylmethyl)-N-[4-methyl-3-[(4-pyridin-3-yl)pyrimidin-2-ylamino)phenyl]benzamide isolated from the reaction mixture contains not more than 2% w/w of the β-crystal form of the methanesulfonic acid addition salt of 4-(4-methylpiperazin-1-ylmethyl)-N-[4-methyl-3-[(4-pyridin-3-yl)pyrimidin-2-ylamino)phenyl]benzamide.

18. The process of claim 17 wherein said α-crystal form of the methanesulfonic acid addition salt of 4-(4-methylpiperazin-1-ylmethyl)-N-[4-methyl-3-[(4-pyridin-3-yl)pyrimidin-2-ylamino)phenyl]benzamide isolated from the reaction mixture contains not more than 1% w/w of the β-crystal form of the methanesulfonic acid addition salt of 4-(4-methylpiperazin-1-ylmethyl)-N-[4-methyl-3-[(4-pyridin-3-yl)pyrimidin-2-ylamino)phenyl]benzamide.

* * * * *